(12) United States Patent
Voets et al.

(10) Patent No.: US 9,194,863 B2
(45) Date of Patent: Nov. 24, 2015

(54) TREATMENT OF PAIN

(75) Inventors: Thomas Voets, Kessel-Lo (BE); Joris Vriens, Wakkerzeel (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 7 days.

(21) Appl. No.: 14/115,034

(22) PCT Filed: May 4, 2012

(86) PCT No.: PCT/BE2012/000023
§ 371 (c)(1),
(2), (4) Date: Oct. 31, 2013

(87) PCT Pub. No.: WO2012/149614
PCT Pub. Date: Nov. 8, 2012

(65) Prior Publication Data
US 2014/0079640 A1    Mar. 20, 2014

(30) Foreign Application Priority Data
May 5, 2011    (GB) .................................. 1107467.1

(51) Int. Cl.
*G01N 33/50* (2006.01)
*A61K 49/00* (2006.01)
*G01N 33/68* (2006.01)

(52) U.S. Cl.
CPC ............ *G01N 33/5023* (2013.01); *A61K 49/00* (2013.01); *G01N 33/6872* (2013.01); *G01N 2500/10* (2013.01); *G01N 2800/2842* (2013.01)

(58) Field of Classification Search
CPC ........................... G01N 33/6872; A61K 49/00
See application file for complete search history.

(56) References Cited

PUBLICATIONS

Naylor et al (British Journal of Pharmacology. 2008; 155:567-573).*
Karali et al (Investigative Ophthalmology & Visual Science. Feb. 2007; 48(2): 509-515).*
Piercy et al (Journal of Diabetes and Its Complications. 1999; 13(3):163-169).*
Hao et al (Anesth Analg. 2003; 96:1065-1071).*
Jain et al (Pharmacological Research. Jun. 2009; 59(6): 385-392).*
Meseguer et al. (Current Pharmaceutical Biotechnology. Methodological Consideration to Understand the Sensory Function of TRP Channels: 2011; 12:3-11).*
International Search Report and Written Opinion of the International Searching Authority for International Application No. PCT/BE2012/000023, mailed on Oct. 23, 2012.
Klose et al., "Fenamates as TRP channel blockers: mefenamic acid selectively blocks TRPM3," *British Journal of Pharmacology*, vol. 162(8), pp. 1757-1769 (Apr. 1, 2011).
Majeed et al., "Pregnenolone sulphate-independent inhibition of TRPM3 channels by progesterone," *Cell Calcium*, vol. 51(1) pp. 1-11 (Jan. 1, 2012).
Okuda et al., "The antinociceptive effects of estradiol on adjuvant-induced hyperalgesia in rats involve activation of adrenergic and serotonergic systems," *Journal of Anesthesia*, vol. 25(3), pp. 392-397 (Apr. 29, 2011).
Ren et al., "Progesterone attenuates persistent inflammatory hyperalgesia in female rats: involvement of spinal NMDA receptor mechanisms," Brain Research, vol. 865(2), pp. 272-277 (May 1, 2000).
Vriens et al., "TRPM3 Is a Nociceptor Channel Involved in the Detection of Noxious Heat," Neuron, vol. 70(3), pp. 482-494 (May 11, 2011).

* cited by examiner

*Primary Examiner* — Scott Long
(74) *Attorney, Agent, or Firm* — Knobbe, Martens, Olson & Bear, LLP

(57) ABSTRACT

The present invention relates to the use of an antagonist of the non-selective cation channel TRPM3 as a medicine for the treatment of pain. The present invention further relates to a method for identification of novel compounds for the treatment of pain, such as TRPM3-antagonists and compounds that modulate the activity or expression of TRPM3. The present invention relates to the use of TRPM3 antagonists as analgesics and the use of the compounds of this invention for the treatment of pain such as but not limited to inflammatory hyperalgesia.

7 Claims, 15 Drawing Sheets

A

B

TREATMENT OF PAIN

CROSS-REFERENCE TO RELATED APPLICATIONS

Figure 1:
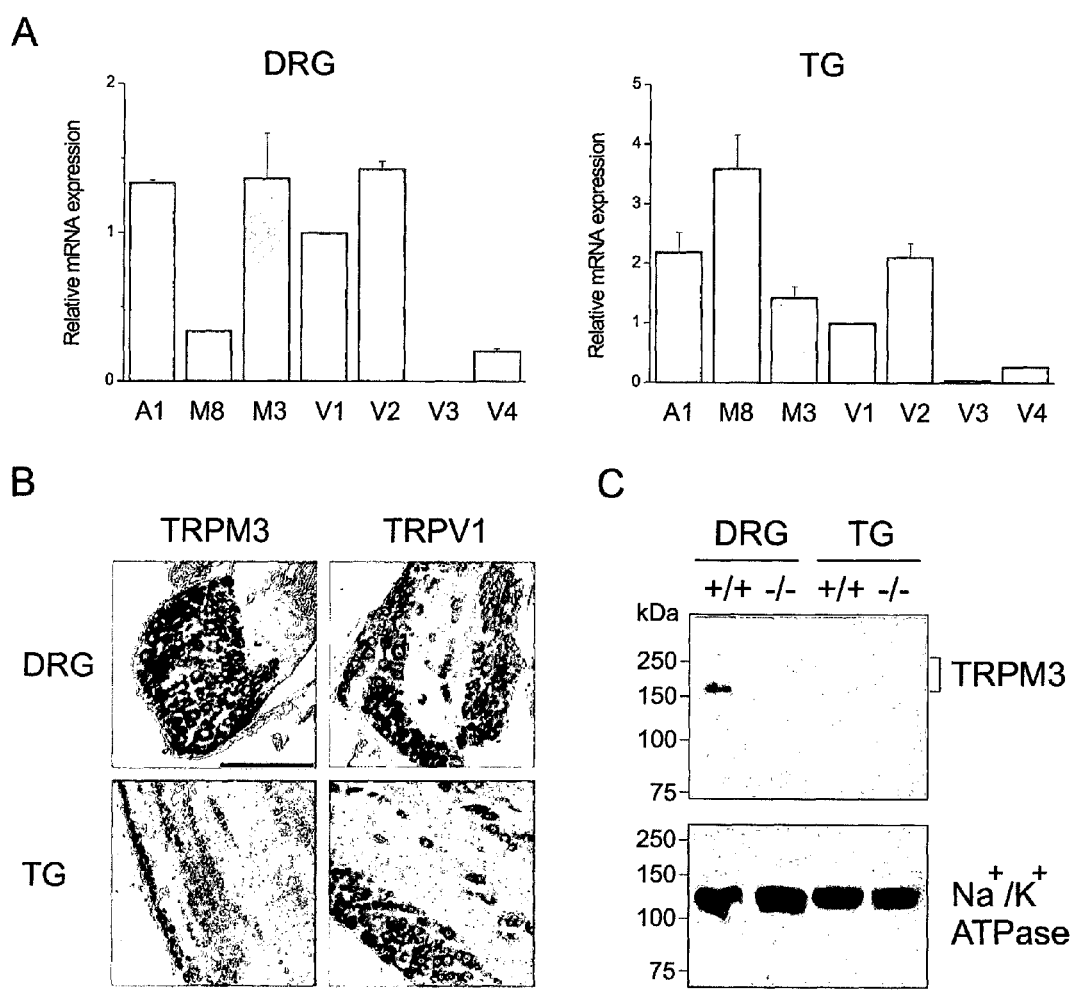

This application is the U.S. National Phase under 35 U.S.C. §371 of International Application PCT/BE2012/000023, filed May 4, 2012, which claims priority to GB 1107467.1, filed May 5, 2011.

FIELD OF THE INVENTION

The present invention relates to the use of an antagonist of the non-selective cation channel TRPM3 as a medicine for the treatment of pain. It further relates to the use of compounds that prevent production of endogenous TRPM3 agonists for the treatment of pain. The present invention further relates to a method for identification of novel compounds for the treatment of pain, such as TRPM3-antagonists and compounds that modulate the activity or expression of TRPM3.

The present invention relates to the use of TRPM3 antagonists as analgesics and the use of the compounds of this invention for the treatment of pain such as but not limited to inflammatory hyperalgesia.

BACKGROUND OF THE INVENTION

The detection and rapid avoidance of noxious thermal stimuli is crucial for survival (Basbaum et al., 2009). Both painful and innocuous thermal stimuli are conveyed by primary afferent sensory neurons that innervate skin and mouth and have their cell bodies in the trigeminal (TG) and dorsal root ganglia (DRG) (Basbaum et al., 2009; Caterina, 2007). Accumulating evidence indicates that the detection of thermal stimuli in mammals strongly depends on the activation of temperature-sensitive non-selective cation channels of the TRP superfamily (Bandell et al., 2007; Basbaum et al., 2009; Caterina, 2007; Talavera et al., 2008). TRPM8 and TRPA1 were shown to be activated by cooling (McKemy et al., 2002; Peier et al., 2002a; Story et al., 2003) and to mediate cold responses in TG and DRG neurons (Bautista et al., 2007; Colburn et al., 2007; Dhaka et al., 2007; Karashima et al., 2009). Consequently, knockout mice lacking either TRPM8 or TRPA1 exhibit specific behavioral deficits in response to cold stimuli (Bautista et al., 2007; Colburn et al., 2007; Dhaka et al., 2007; Kwan et al., 2006; Nilius and Voets, 2007), although the involvement of TRPA1 in cold sensing in vivo remains a matter of debate (Bautista et al., 2006; Karashima et al., 2009; Knowlton et al., 2010; Kwan et al., 2006). Oppositely, four members of the TRPV subfamily, TRPV1-4, are activated upon heating (Caterina et al., 1999; Caterina et al., 1997; Chung et al., 2003; Guler et al., 2002; Peier et al., 2002b; Smith et al., 2002; Watanabe et al., 2002; Xu et al., 2002). TRPV1, a heat and capsaicin sensor expressed in nociceptor neurons is involved in detecting heat-evoked pain, particularly in inflamed tissue (Caterina et al., 2000; Caterina et al., 1997; Davis et al., 2000; Tominaga et al., 1998). The related TRPV3 and TRPV4 are strongly expressed in skin keratinocytes, and have been mainly implicated in sensing innocuously warm temperatures (Chung et al., 2003; Chung et al., 2004; Lee et al., 2005; Moqrich et al., 2005; Peier et al., 2002b; Smith et al., 2002; Xu et al., 2002). TRPV2 is activated by extreme heat (>50° C.) (Caterina et al., 1999), and has been considered as a potential molecular candidate to explain the activation of TRPV1-deficient sensory neurons at temperatures above ~50° C., as well as the residual nocifensive response to noxious heat stimuli in TRPV1-deficient mice (Caterina et al., 2000). However, it remains to be established whether TRPV2 functions as a thermosensor in vivo, as deficits in detecting noxious heat have not yet been described for TRPV2-deficient mice. Moreover, it has been clearly demonstrated that a large fraction of heat-sensitive nociceptors lack expression of both TRPV1 and TRPV2 (Woodbury et al., 2004). Thus, the molecular basis of TRPV1-independent noxious heat sensing in the somatosensory system is currently unknown (Basbaum et al., 2009).

TRPM3 is a member of the melastatin subfamily of TRP channels with limited homology to the heat-sensitive TRPV channels. It is expressed in a variety of neuronal and non-neuronal tissue (Grimm et al., 2003; Lee et al., 2003; Oberwinkler and Philipp, 2007). The TRPM3 gene encodes for different TRPM3 isoforms due to alternative splicing and exon usage, leading to channels with divergent pore and gating properties (Oberwinkler et al., 2005). The neurosteroid pregnenolone sulphate (PS) is currently the most potent known activator of TRPM3 (in casu, the (2 isoform, Wagner et al., 2008), and PS-induced activation of TRPM3-like currents has been linked to vascular smooth muscle contraction and $Ca^{2+}$-induced insulin release from pancreatic islets in vitro (Naylor et al., 2010; Wagner et al., 2008). However, it is currently unclear whether PS-induced gating of TRPM3 is occurring in vivo, and the physiological roles of the channel remain largely unclear (Nilius and Voets, 2008).

Previous studies demonstrating expression of TRPM3-encoding mRNA in sensory neurons (Lechner et al., 2009; Nealen et al., 2003; Staaf et al., 2010), and PS-induced pain responses in mice (Ueda et al., 2001) encouraged us to investigate the possible role of TRPM3 in somatosensation and nociception. In this study we found that TRPM3 is functionally expressed in a large subset of sensory neurons from the dorsal root and trigeminal ganglia (DRG and TG), and accounts for the majority of PS responses in these cells. Intraplantar injection of PS evokes nocifensive responses in wild type mice but not in Trpm3$^{-/-}$ mice, indicating that TRPM3 activation provokes pain. Moreover, we discovered that TRPM3 is activated by heat. Consequently, TRPM3-deficient mice exhibit clear deficits in their avoidance response to noxious heat, but not to noxious cold or mechanical stimuli. TRPM3-deficient mice also failed to develop heat hyperalgesia following an inflammatory challenge. Our results provide evidence that TRPM3 plays a previously unanticipated role in heat sensation and nociception.

SUMMARY OF THE INVENTION

The present invention is based on the finding that the Transient Receptor Potential Melastatin-3 (TRPM3) is a nociceptor channel implicated in the detection of pain. It was shown that TRPM3, molecularly and functionally expressed in sensory neurons, functions as a chemo- and thermosensor in the somatosensory system and mediates nocifensive behavioral responses. Interfering with the TRPM3 function, e.g. by TRPM3-antagonistic agents and/or agents that reduce the expression of TRPM3 can be used as an analgetic treatment and/or prophylaxis of pain or the perception of pain. Therefore, a first aspect of the present invention relates to the use of an agent in the manufacture of a medicament for the treatment and/or prophylaxis of pain, wherein said agent is selected from the list consisting of: an agent which is a TRPM3 antagonist or a pharmaceutically acceptable derivative thereof; an agent which interferes with and preferentially inhibits the production of endogenous TRPM3-activating messengers; an agent which interferes with and preferentially inhibits the activity of TRPM3-expressing sensory neurons and an agent which inhibits expression of the gene encoding TRPM3 or a pharmaceutically acceptable derivative thereof.

A second aspect of the present invention provides a method for the treatment and/or prophylaxis of pain, said method comprising the administration of an effective, non-toxic and pharmaceutically acceptable amount of an agent selected from the list consisting of: an agent which is a TRPM3 antagonist or a pharmaceutically acceptable derivative thereof; an agent which interferes with and preferentially inhibits the production of endogenous TRPM3-activating messengers; an agent which interferes with and preferentially inhibits the activity of TRPM3-expressing sensory neurons; and an agent which inhibits expression of the gene encoding TRPM3 or a pharmaceutically acceptable derivative thereof.

In a third aspect the present invention provides a pharmaceutical composition for the treatment and/or prophylaxis of pain, whose composition comprises an agent selected from the list consisting of: an agent which is a TRPM3 antagonist or a pharmaceutically acceptable derivative thereof; an agent which interferes with and preferentially inhibits the production of endogenous TRPM3-activating messengers; an agent which interferes with and preferentially inhibits the activity of TRPM3-expressing sensory neurons; and an agent which inhibits expression of the gene encoding TRPM3 or a pharmaceutically acceptable derivative thereof.

In a fourth aspect the present invention provides the use of an agent in the treatment and/or prophylaxis of pain, wherein said agent is selected from the list consisting of: an agent which is a TRPM3 antagonist or a pharmaceutically acceptable derivative thereof; an agent which interferes with and preferentially inhibits the production of endogenous TRPM3-activating messengers; an agent which interferes with and preferentially inhibits the activity of TRPM3-expressing sensory neurons; and an agent which inhibits expression of the gene encoding TRPM3 or a pharmaceutically acceptable derivative thereof.

A fifth aspect of the present invention relates to a method for the identification of an agent for the treatment and/or prophylaxis of pain, wherein said method comprises screening for agents capable of inhibiting TRPM3. In a particular embodiment, said method for the identification of an agent for the treatment and/or prophylaxis of pain comprises the screening for agents capable of interfering with and preferentially inhibiting or blocking the TRPM3 signaling cascade. In another particular embodiment, said method for the identification of an agent for the treatment and/or prophylaxis of pain comprises the screening for agents capable of inhibiting expression of the gene encoding TRPM3.

In certain embodiments of the present invention, the treatment of pain is the treatment and/or prophylaxis of pain associated with any disease or condition. In particular embodiments of this invention, the pain or condition or disease for which treatment and/or prophylaxis is envisaged is hyperalgesia. In other particular embodiments, the pain or condition or disease for which treatment and/or prophylaxis is envisaged is an inflammatory-related disease or condition such as but not limited to inflammatory hyperalgesia.

Certain embodiments of the present invention relate to a method for modulating, preferentially inhibiting or diminishing, the perception of pain in a subject, wherein said method comprises administering to said subject an affective amount of an agent selected from the list consisting of: an agent which is a TRPM3 antagonist or a pharmaceutically acceptable derivative thereof; an agent which interferes with and preferentially inhibits the production of endogenous TRPM3-activating messengers; an agent which interferes with and preferentially inhibits the activity of TRPM3-expressing sensory neurons; and an agent which inhibits expression of the gene encoding TRPM3 or a pharmaceutically acceptable derivative thereof. In more particular embodiments, said method for modulating, preferentially inhibiting or diminishing, the perception of pain in a subject is a method wherein decreasing the level of or the activity of TRPM3 changes, preferentially inhibits or diminishes, the perception of pain in a subject.

In certain embodiments of the present invention the agent of this invention is selected from the list consisting of: an agent which is a TRPM3 antagonist or a pharmaceutically acceptable derivative thereof; an agent which interferes with and preferentially inhibits the production of endogenous TRPM3-activating messengers; an agent which interferes with and preferentially inhibits the activity of TRPM3-expressing sensory neurons; and an agent which inhibits expression of the gene encoding TRPM3 or a pharmaceutically acceptable derivative thereof. In certain embodiments of the present invention said agent is a small molecule, an antisense oligonucleotide, an aptamer, a small interfering RNA or RNAi molecule, a soluble receptor, a ribozyme or an antibody. In certain embodiments of the present invention the agent of this invention is a TRPM3 antagonist or a pharmaceutically acceptable derivative thereof. In more specific embodiments of this invention, said TRPM3 antagonist is an antibody, a small molecule, an aptamer or a soluble receptor and in further specific embodiments said TRPM3 antagonist is a TRPM3 antibody or a TRPM3 aptamer. In other particular embodiments of the present invention, the agent of this invention is an agent that inhibits expression of the gene encoding TRPM3, such as but not limited to an antisense oligonucleotide, an aptamer, a small interfering RNA or RNAi agent, a small molecule and a ribozyme, or a pharmaceutically acceptable derivative thereof. In further specific embodiments of this invention, said agent that inhibits expression of the gene encoding TRPM3 is a TRPM3 RNAi molecule or a TRPM3 aptamer. In other particular embodiments of the present invention, the agent of this invention is an agent that inhibits expression of the gene encoding an agonist of TRPM3, such as but not limited to an antisense oligonucleotide, an aptamer, a small interfering RNA or RNAi agent, a small molecule and a ribozyme, or a pharmaceutically acceptable derivative thereof.

In certain embodiments of the present invention, the subject is a mammal. In other embodiments of the present invention, the subject is a primate. In other embodiments of the present invention, the subject is a human. In yet other embodiments of the present invention, the subject is a laboratory test animal.

In certain embodiments of the present invention, the medicament is for the control of pain, more particularly the control of pain in a subject, preferentially a human.

The present invention further relates to a method of treating or preventing symptoms associated with pain or sensation or perception of pain in a subject, more particularly said method comprising administering to said subject an effective amount of an agent of this invention, preferentially for a time and under conditions to ameliorate one or more symptoms, e.g. symptoms associated with pain or a disease or condition associated with pain. In a more particular embodiment such symptoms are associated with the sensation or perception of pain and in another particular embodiment such symptoms are associated with inflammatory disease conditions, such as but not limited to inflammatory hyperalgesia.

In certain embodiments of this invention, hyperalgesia is primary hyperalgesia, secondary hyperalgesia or opioid-induced hyperalgesia.

Certain embodiments of the present invention relate to a pharmaceutical composition comprising an agent of this invention and one or more pharmaceutically acceptable carriers and/or diluents.

In certain embodiments of the present invention inflammatory-related disease or condition is inflammation, inflammatory hyperalgesia, acne, angina, arthritis, aspiration pneumonia, empyema, gastroenteritis, intestinal flu, necrotizing enterocolitis, pelvic inflammatory disease, pharyngitis, pleurisy, raw throat, rubor, sore throat, stomach flu and urinary tract infections, Chronic Inflammatory Demyelinating Polyneuropathy, Chronic Inflammatory Demyelinating Polyradiculoneuropathy, Chronic Inflammatory Demyelinating Polyneuropathy or Chronic Inflammatory Demyelinating Polyradiculoneuropathy.

DESCRIPTION

Brief Description of the Figures of the Invention

FIG. 1. TRPM3 is Expressed in Somatosensory Neurons (A) Quantitative RT-PCR showing the mRNA expression of the indicated TRP channels (relative to TRPV1) in isolated DRG (left) and TG (right) neurons (n=3 independent experiments).

(B) In situ hybridisation using specific antisense RNA probes for detection of TRPM3 and TRPV1 mRNA in tissue sections of DRG (upper panels) and TG (lower panels). Sense probes did not reveal any specific staining (see FIG. 9). Scale bar represents 100 µm.

(C) Western blot of total membrane fractions isolated from DRG and TG tissues of Trpm3$^{+/+}$ (+/+) and Trpm3$^{-/-}$ mice using a TRPM3-specific antibody. Detection of Na$^+$/K$^+$ ATPase was used as a control of equal loading of protein samples (30 □g/lane). Data are represented as mean±SEM.

Figure 2:
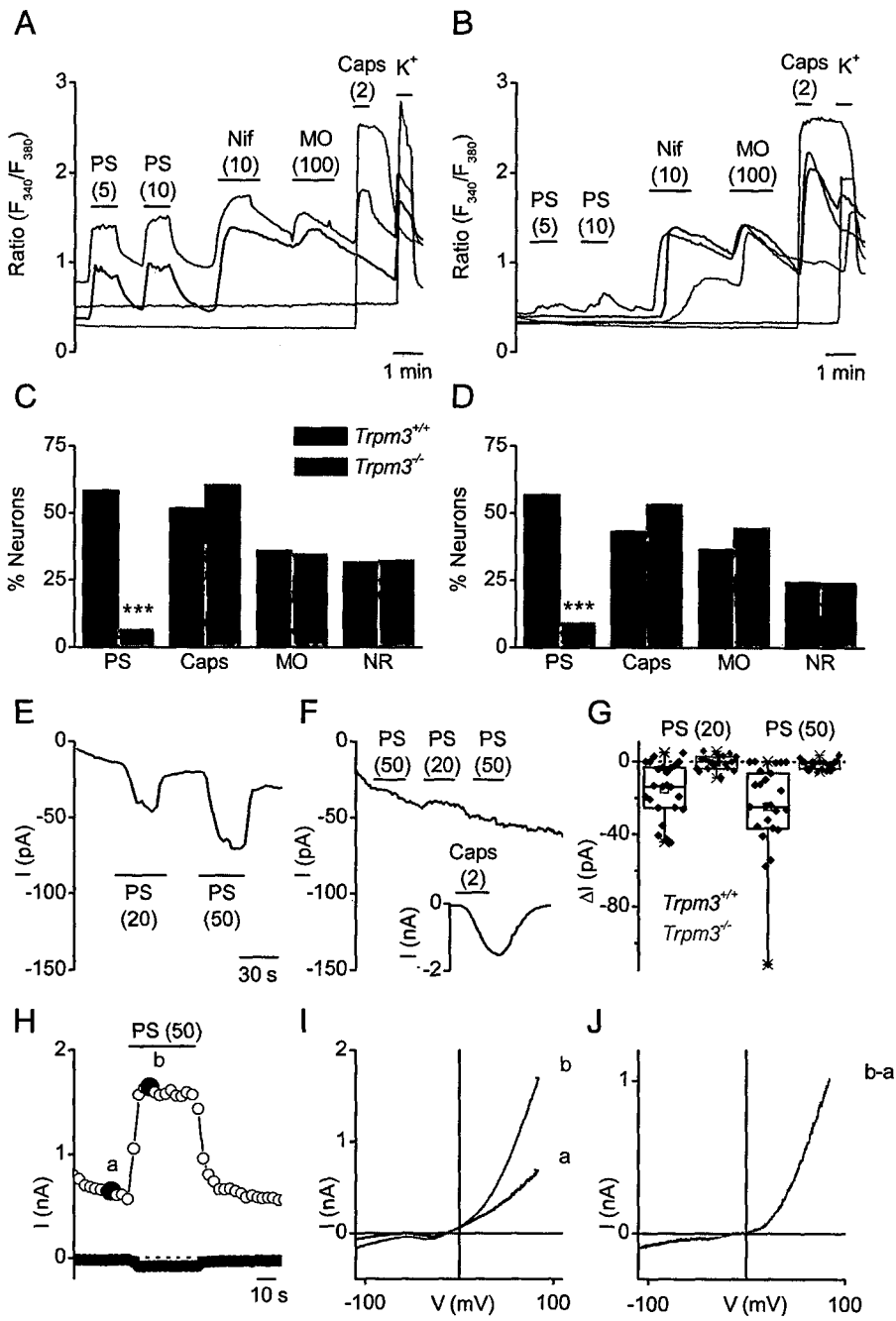

FIG. 2. Reduced PS Responses in TRPM3-Deficient Sensory Neurons (A-B) Representative traces showing typical patterns of intracellular Ca$^{2+}$ in DRG neurons from Trpm3$^{+/+}$ (A) and Trpm3$^{-/-}$ (B) mice in response to pregnenolone sulphate (PS, 5 µM and 10 µM), nifedipine (Nif, 10 µM), mustard oil (MO, 100 µM), capsaicin (caps, 2 µM) and (50 mM).

(C-D) Prevalence of dorsal root ganglion (C) and trigeminal (D) neurons responsive to PS (10 µM), caps, MO or non-responsive to these three stimuli (NR) in Trpm3$^{+/+}$ (Black, n=303 for DRG and n=273 for TG) and Trpm3$^{-/-}$ mice (gray, n=356 for DRG and n=320 for TG). ***, P<0.001 (Fisher's exact test).

(E-F) Time course of the inward whole-cell current at −40 mV in TG neurons from Trpm3$^{+/+}$ (E) and Trpm3$^{-/-}$ (F) mice upon stimulation with pregnenolone sulphate (PS, 20 µM and 50 µM) or capsaicin (2 µM, inset F).

(G) PS-activated currents (20 µM and 50 µM) at −40 mV in individual TG neurons from Trpm3$^{+/+}$ and Trpm3−/− (gray) mice. Box plot indicates the mean as well as the 10, 25, 75 and 90% percentiles.

(H) Amplitude of currents at a holding potential of +80 and −80 mV (measured with voltage ramps) during application of 50 µM PS in a Trpm3$^{+/+}$ DRG neuron in Na$^+$-free solution.

(I) Current-voltage relationship before (black) and during (red) application of PS (50 µM). Time points are indicated in panel (H).

(J) Current-voltage relationship of the PS-induced current obtained as the difference between the two traces in panel (I). Note that the current is steeply outwardly rectifying and displays a reversal potential close to 0 mV, in agreement with the characteristics of heterologously expressed TRPM3 channels.

Figure 3:
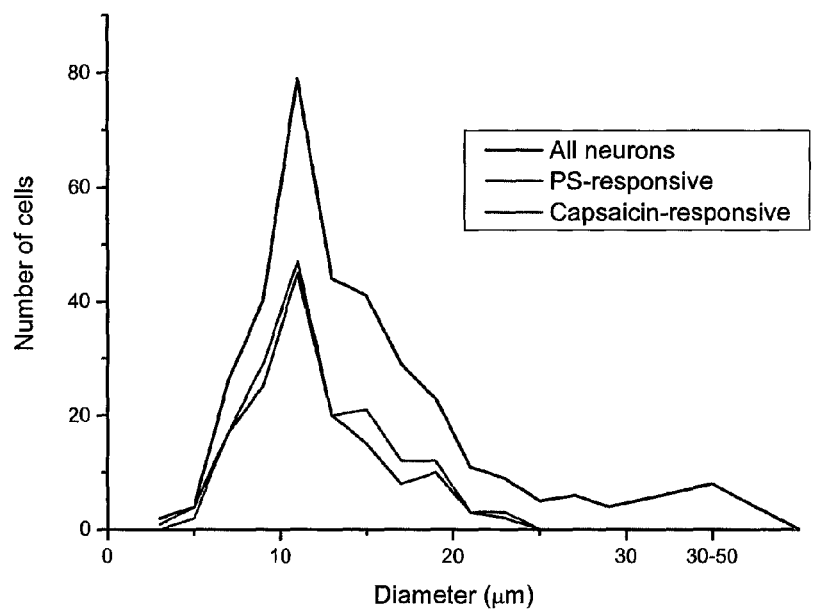

FIG. 3. PS Responsiveness is Limited to Small-Diameter DRG Neurons

Shown is a size distribution of a total population of DRG neurons, and of the subpopulation of capsaicin-sensitive (red) and PS-sensitive (green)neurons. PS responses were restricted to neurons with a diameter <25 µm (average diameter: 12.4±0.3 µm), similar the size of capsaicin-responsive neurons (average diameter: 12.0±0.3 µm).

Figure 4:
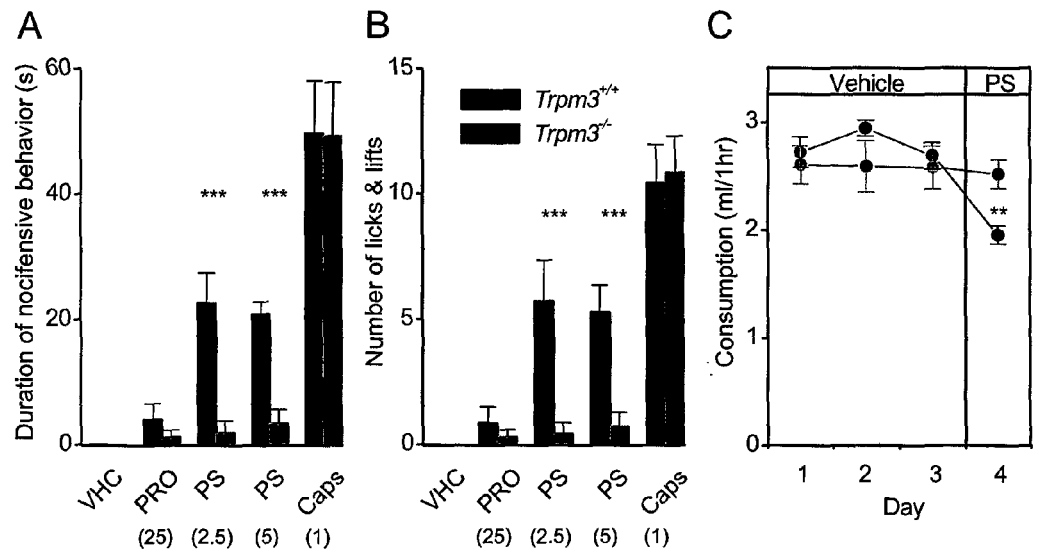

FIG. 4. Nocifensive and Aversive Responses to PS (A-B) Total duration of nocifensive behavior (A) and number of behavioral responses (paw licks and lifts in 2 minutes; (B) in response to intraplantar injection of vehicle (VHC), progesterone (PRO, 20 nmol/paw), pregnenolone sulphate (PS, 2.5 or 5 nmol/paw) or capsaicin (caps, 1 nmol/paw) in Trpm3$^{+/+}$ and Trpm3$^{-/-}$ mice (n=8 for each genotype).

(C) Effect of addition of PS to the drinking water on water consumption in Trpm3$^{+/+}$ and Trpm3$^{-/-}$ mice (n=6 for each genotype). , P<0.01, *P<0.001 (two sample t-test). Data are represented as mean±SEM.

Figure 5:
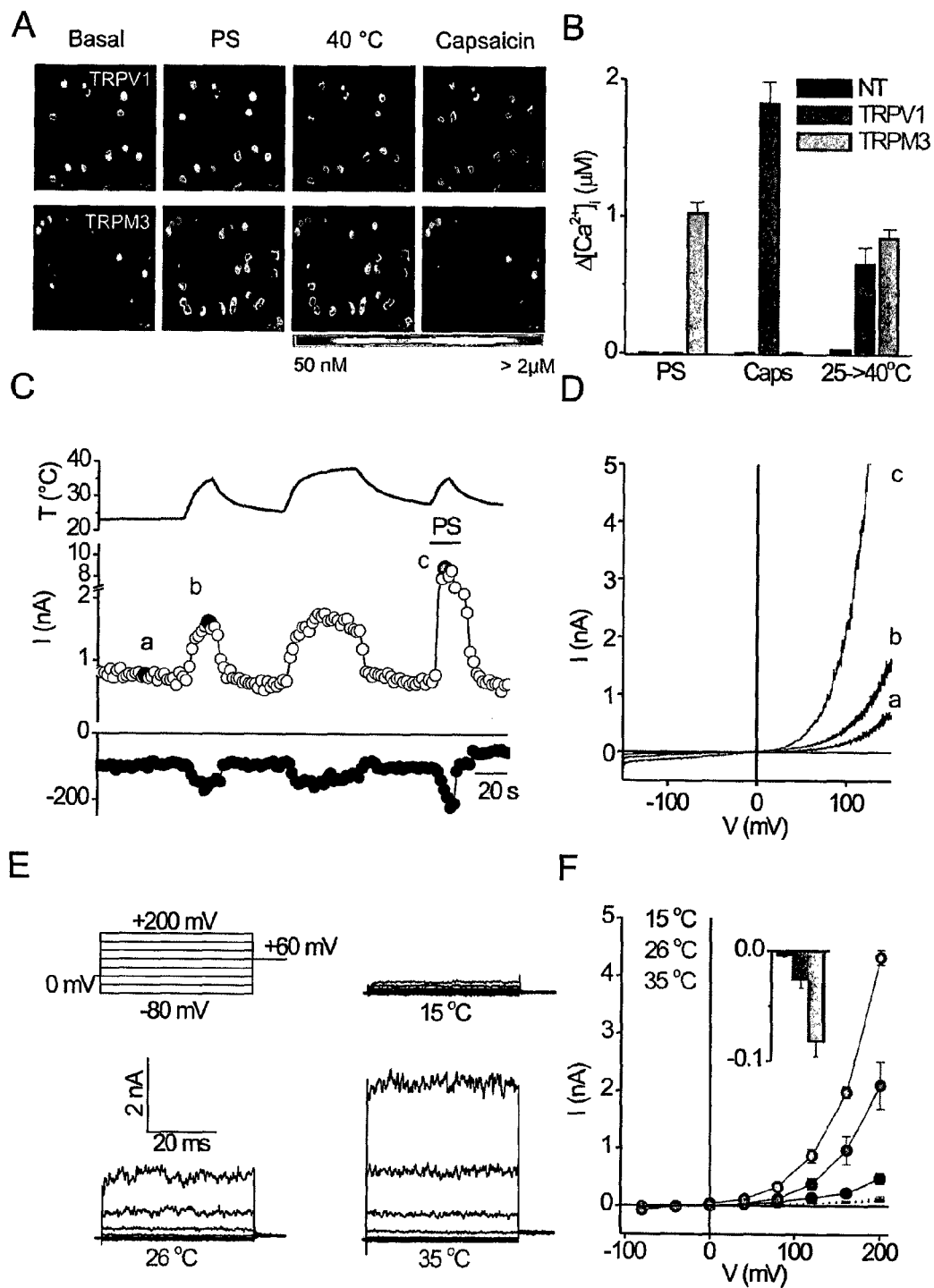

FIG. 5. TRPM3 is a Heat Sensitive Channel (A) Comparison of intracellular Ca$^{2+}$ responses to PS (20 µM), capsaicin (2 µM) and heat (rapid increase in temperature from 25 to 40° C.) in HEK293T cells transiently transfected with TRPV1 (top) or TRPM3 (the TRPM3α2 isoform) (bottom). Pseudocolor images of Fura-2 loaded cells; scale bar shows intracellular calcium concentration. Green circles indicate transfected cells, as evidenced by GFP fluorescence.

(B) Calcium increase induced by PS, capsaicin and heat in non transfected (NT, black n=39) HEK293T cells, and in HEK293T cells transiently transfected with TRPV1 (red, n=31) or TRPM3 (green, n=29).

(C) Time course of whole-cell currents at +150 and −150 mV in TRPM3-transfected HEK293T cells stimulated with heat and PS (50 µM).

(D) Representative current-voltage relations obtained from time points indicated in (C).

(E) Representative whole-cell TRPM3 currents recorded during voltage steps ranging from −80 to +200 mV at the indicated temperatures.

(F) Average steady-state current amplitudes at the indicated temperatures. Non transfected cells are indicated as dotted lines. Data are represented as mean±SEM.

Figure 6:
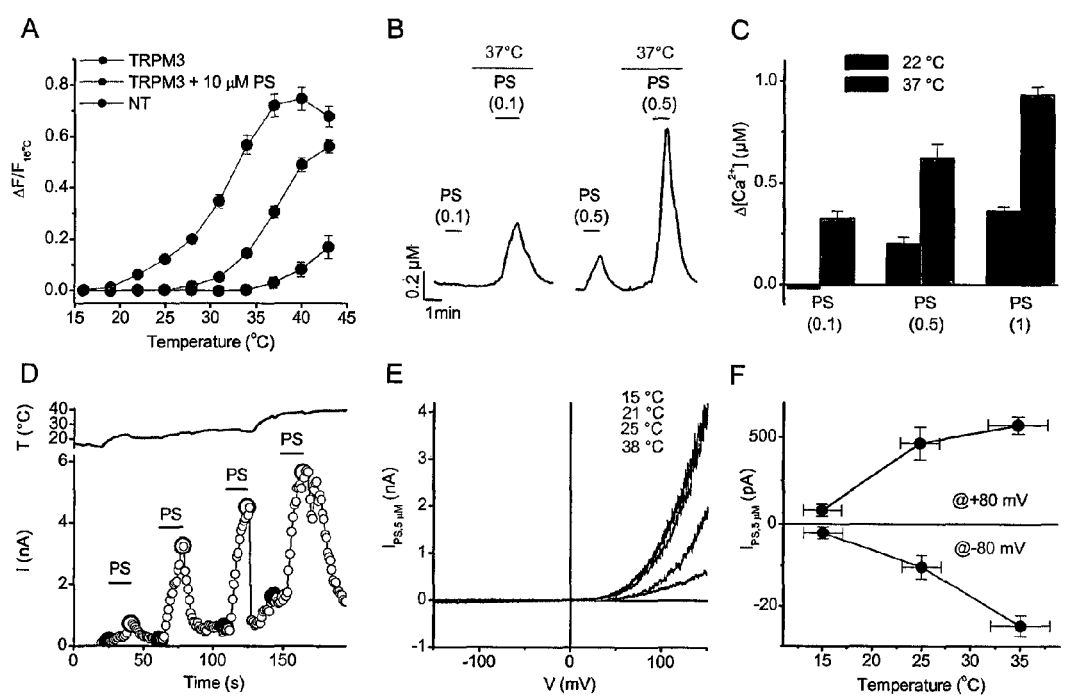

FIG. 6. Synergistic Effects of Heat and PS on TRPM3

(A) Relative changes in Fluo-4 fluorescence in response to a gradual temperature increase form 16 to 43° C. in HEK293T stably expressing TRPM3 in the absence and presence of 10 µM PS, and in non transfected HEK293T cells. PS did not affect the heat response of non transfected HEK293T cells (data not shown). Expression level of TRPM3 in stably expressing TRPM3 cells is shown in FIG. 9B.

(B) Typical examples of the intracellular calcium increase induced by low doses of PS (100 and 500 nM) applied at room temperature (22° C.) and 37° C. in HEK293T cells stably expressing TRPM3.

(C) Bar diagram showing average Ca$^{2+}$ increases in response to the indicated PS concentrations applied at room temperature (black) and 37° C. (red) (n≥35). Data are represented as mean±SEM.

(D) Time course of whole-cell current responses at +150 mV to a low dose of PS (5 µM) applied at different temperatures.

(E) Current-voltage relations of PS-induced current at different temperatures, determined as the difference between currents obtained at the time points indicated by the coloured circles (open circles minus closed circles).

(F) Temperature dependence of the current amplitude activated by PS (5 μM; n=5). Data are represented as mean±SEM.

Figure 7:
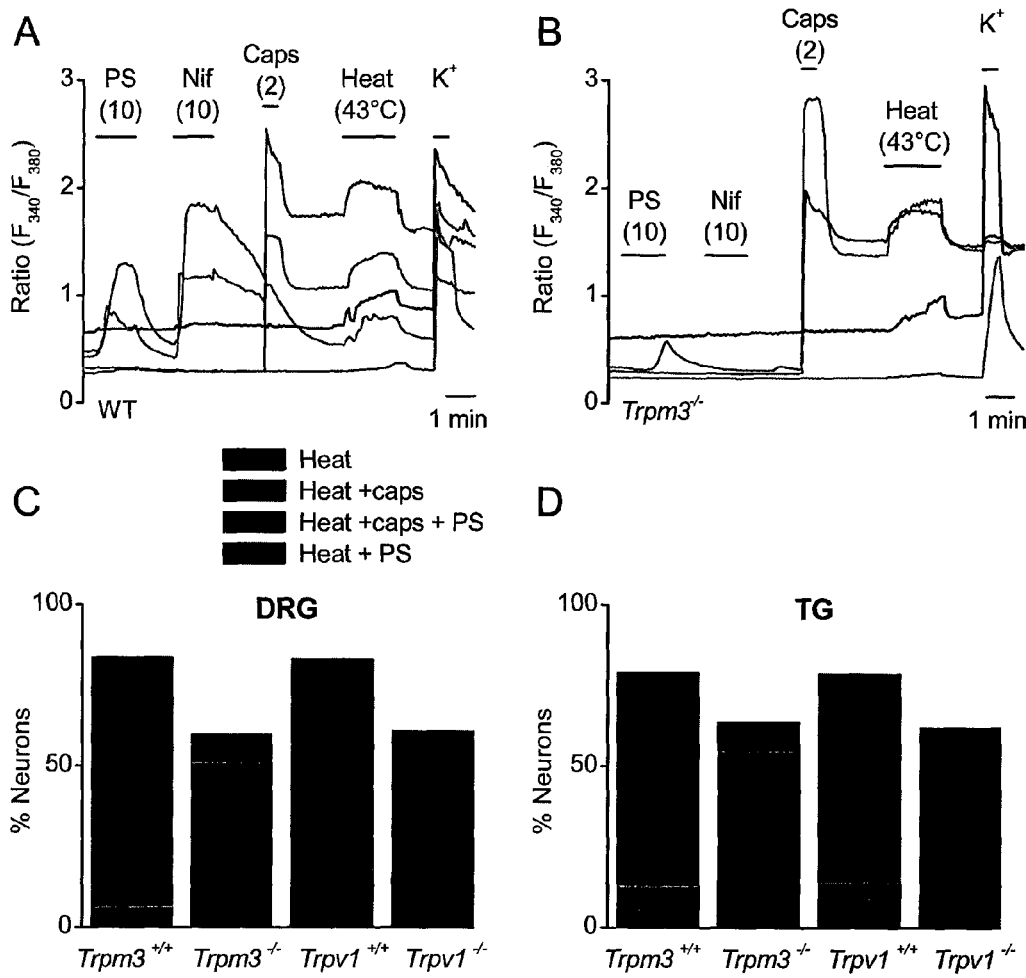

FIG. 7. TRPM3-Dependent Heat Responses in Somatosensory Neurons (A-B) Representative traces showing typical patterns of intracellular $Ca^{2+}$ in TG neurons from Trpm3$^{+/+}$ (A) and Trpm3$^{-/-}$ (B) mice in response to pregnenolone sulphate (PS, 10 μM), nifedipine (Nif, 10 μM), capsaicin (caps, 2 μM), heat (43° C.) and $K^+$ (50 mM).

(C-D) Percentage of DRG (C) and TG (D) neurons responding to heat in preparations from Trpm3$^{+/+}$ (n=135 for DRG and n=159 for TG), TRPM3$^{-/-}$ (n=217 for DRG and n=237 for TG), TRPV1$^{+/+}$ (n=132 for DRG and n=106 for TG) and TRPV1$^{-/-}$ (n=191 for DRG and n=105 for TG) mice. Different colors correspond to the different subtypes of heat responders based on PS and capsaicin sensitivity.

Figure 8:
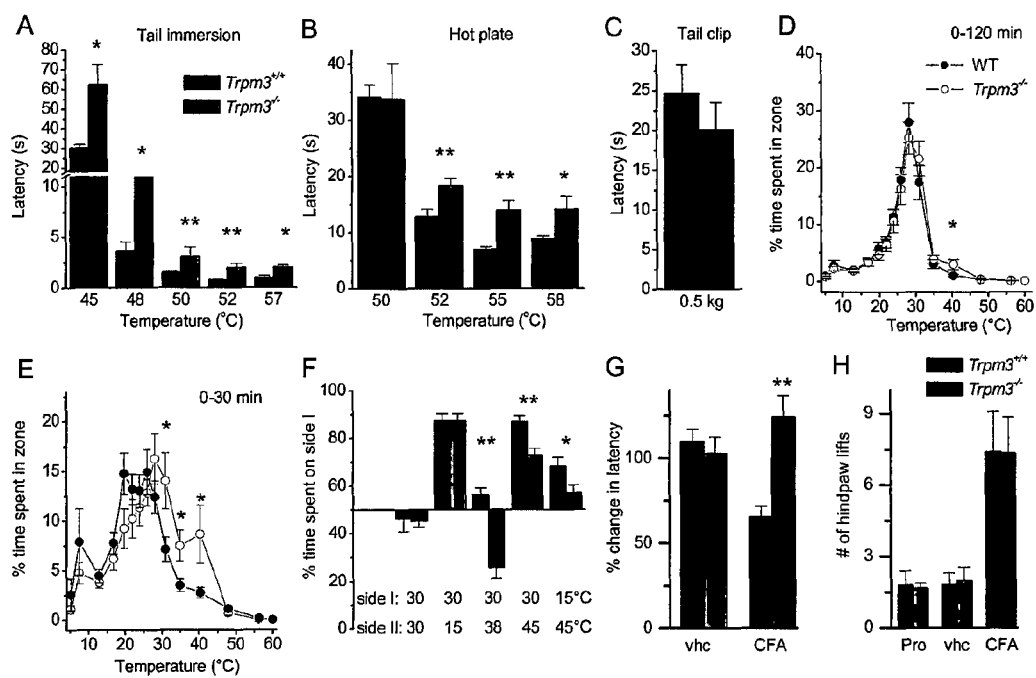

FIG. 8. Impaired Behavioral Responses to Noxious Heat in Trpm3$^{-/-}$ Mice (A-C) Response latencies for Trpm3$^{+/+}$ and Trpm3$^{-/-}$ mice in tail immersion (n=10 for each genotype), hot plate (n=7 for each genotype) and tail clip (n=8 for each genotype) tests. *, P<0.05; **, P<0.01; two-sample t-test.

(D) Comparison of the behavior of Trpm3$^{+/+}$ (n=13) and Trpm3$^{-/-}$ (n=12) mice on the gradient during the entire duration of the experiment (120 min). Trpm3$^{+/+}$ and Trpm3$^{-/-}$ mice show similar preferred temperature zones.

(E) Comparison of the behavior of Trpm3$^{+/+}$ (n=13) and Trpm3$^{-/-}$ (n=12) mice on the gradient during the first 30 min of the experiment.

(F) Comparison of the behavior of Trpm3$^{+/+}$ (n=16) and Trpm3$^{-/-}$ (n=19) mice in the two-temperature choice test, with plates set at the indicated temperatures. Percentage of time mice spent on Side I. *, P<0.05; **, P<0.01 (two-sample t-test). Data are represented as mean±SEM.

(G-H) Change in hot plate latency (G) and cold plate response (H) 24 h after interplanetary CFA injection in Trpm3$^{+/+}$ (black) and Trpm3$^{-/-}$ (gray) (n=6 for each genotype; **, P<0.01 for vehicle versus CFA injection; two-sample t-test).

Figure 9:
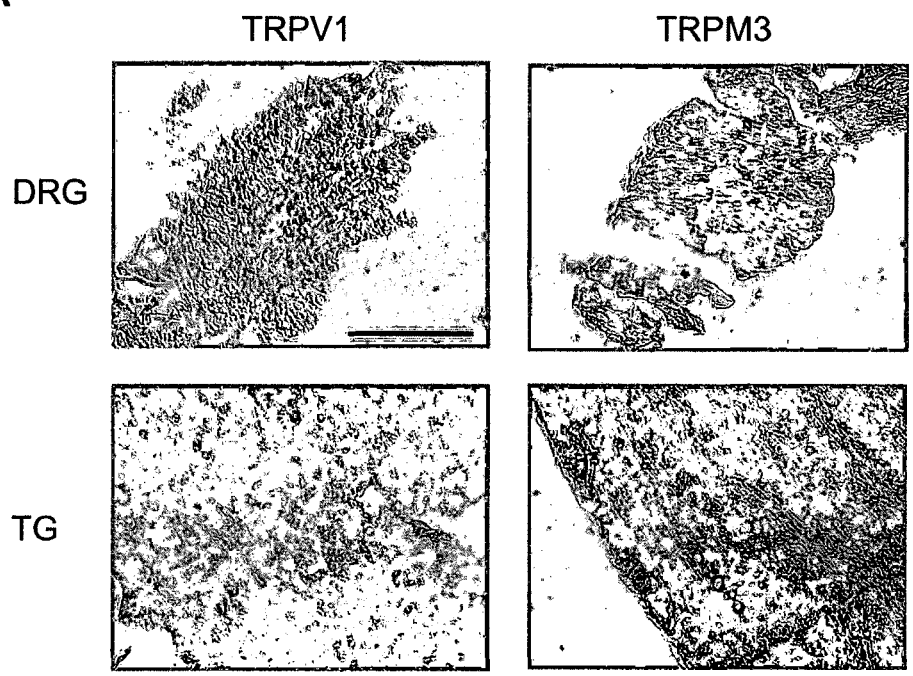
Figure 9:
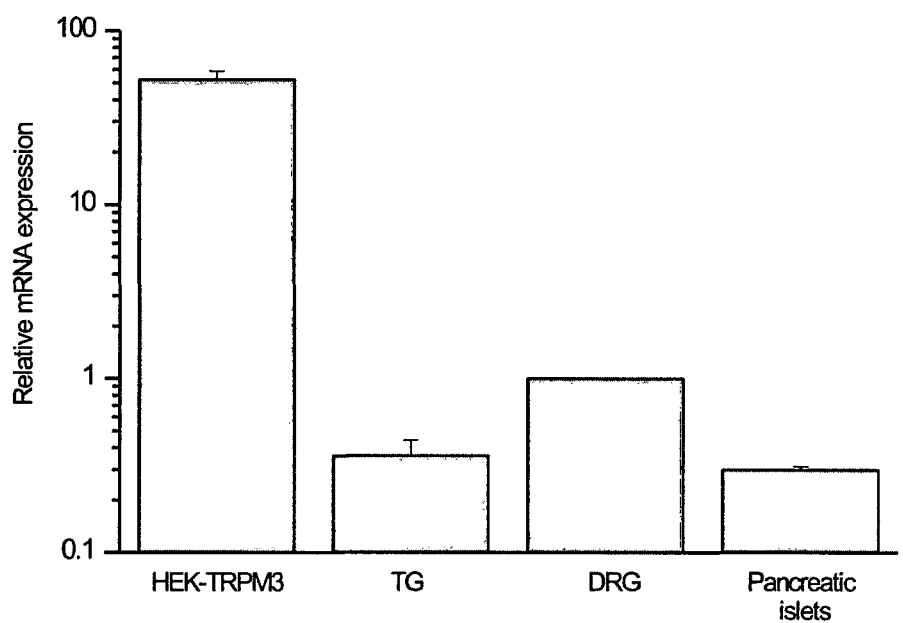

FIG. 9. Control Experiments for TRPM3 mRNA Expression (A) In situ hybridization using sense RNA probe against TRPV1 and TRPM3 mRNA in tissue sections of DRG (upper part) and TG (lower part). Scale bar represents 50 μm.

(B) Quantitative real time PCR showing the mRNA expression of TRPM3 in HEK293 cells stably expressing TRPM3, in isolated TG, DRG and pancreatic islets (n=2 independent experiments). Data represent relative RNA expressing units calibrated for endogenous expression of TRPM3 in DRG.

Figure 10:
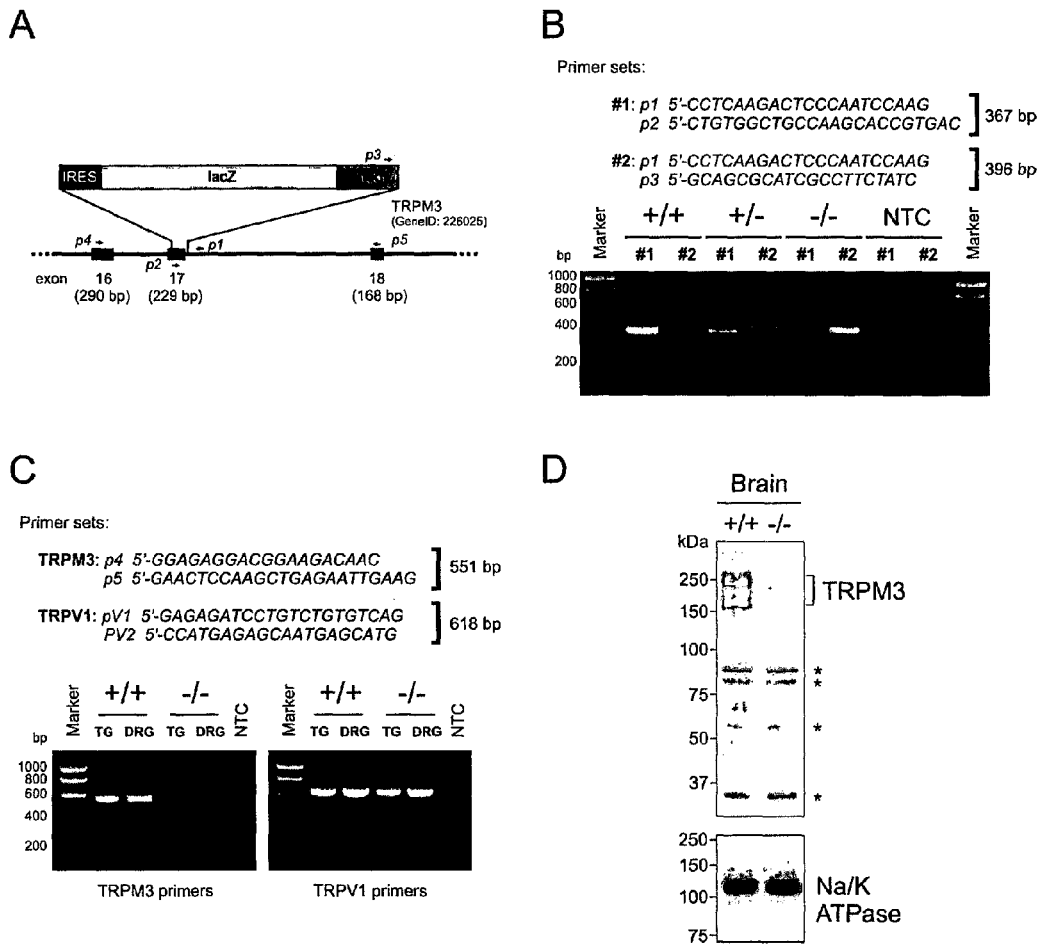

FIG. 10. Generation of TRPM3 Knockout Mice (A) Schematic representation of targeting strategy used for generating Trpm3$^{-/-}$ mice. A cassette containing a β-geo fusion construct flanked by a 5'-terminal IRES sequence was inserted into exon 17 of the mTRPM3 gene by means of homologous recombination.

(B) PCR on genomic DNA obtained from Trpm3$^{+/+}$, Trpm3$^{+/-}$ and Trpm3$^{-/-}$ mice using two different primer pairs. Nucleotide sequence of the primers and predicted amplicon lengths are annotated. Specific positions of primer sets in the genomic sequence are indicated by small arrows in the panel A. Lanes 8 and 9 show no template controls (NTC) for each primer set.

(C) Reverse transcriptase (RT)-PCR analysis of TRPM3 expression in wild type (WT) and Trpm3$^{-/-}$ mice. PCR with Trpm3- and Trpv1-specific primers on cDNA generated by RT reactions from total RNA of TG and DRG tissues isolated from WT and Trpm3$^{-/-}$ mice. Nucleotide sequence of the primers and predicted amplicon lengths are annotated. Trpm3-specific primers are indicated by small arrows in panel A.

(D) Immunodetection of TRPM3 proteins in total membrane fractions isolated from brains of wild type (+/+) and Trpm3$^{-/-}$ mice. Detection of $Na^+/K^+$ ATPase was used as a control of equal loading of protein samples (13 μg/lane). Asterisks indicate nonspecific bands detected in both groups.

Figure 11:
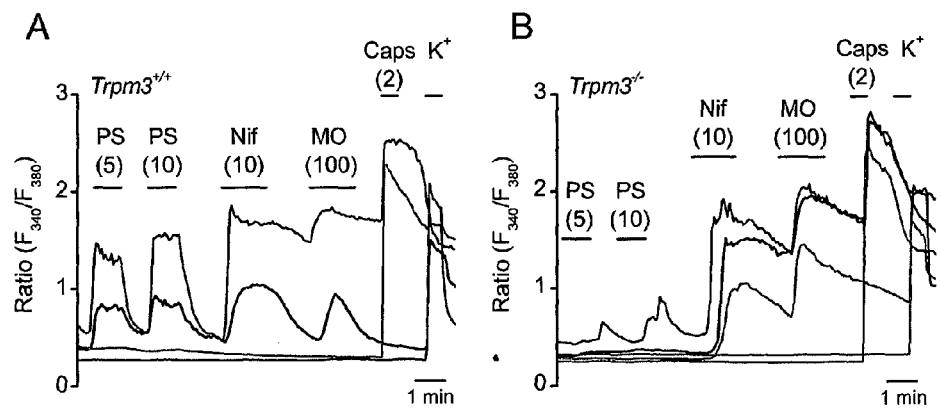

FIG. 11. TRPM3-Dependent PS Responses in TG Neurons (A-B) Representative traces of isolated trigeminal neurons isolated from Trpm3$^{+/+}$ (A) and Trpm3$^{-/-}$ (B) mice were exposed to pregnenolone sulphate (PS; 5 μM and 10 μM), nifedipine (Nif, 10 μM), mustard oil (MO, 100 μM), capsaicin (caps, 2 μM) and $K^+$ (50 mM), responses were assessed by calcium imaging.

Figure 12:
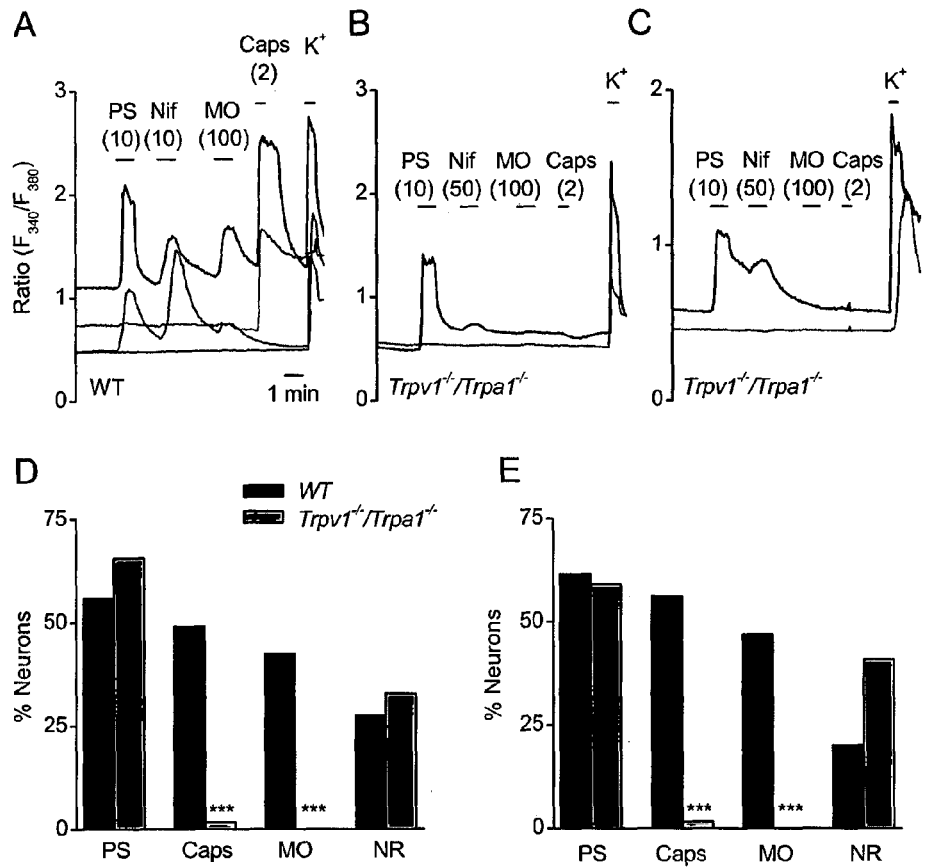

FIG. 12. Effect of PS is Conserved in Trpv1$^{-/-}$/Trpa1$^{-/-}$ Double Knockout (A-C) Representative traces of DRG neurons (A and B) and TG neurons (C) isolated from WT (A) and Trpv1$^{-/-}$/Trpa1$^{-/-}$ double knockout (B and C) mice. Somatosensory neurons were exposed to pregnenolone sulphate (PS, 10 μM), nifedipine (Nif, 50 μM), mustard oil (MO, 100 μM), capsaicin (caps, 2 μM) and high $K^+$ (50 mM) containing solution.

(D-E) Prevalence of DRG (D) and TG (E) neurons responsive to PS (10 μM), caps, MO or non-responsive to these three stimuli (NR) in wild-type (black bars, n=134) or Trpv1$^{-/-}$/Trpa1$^{-/-}$ double knockout (cyan bars, n=101). ***, P<0.001 (Fisher's exact test).

Figure 13:
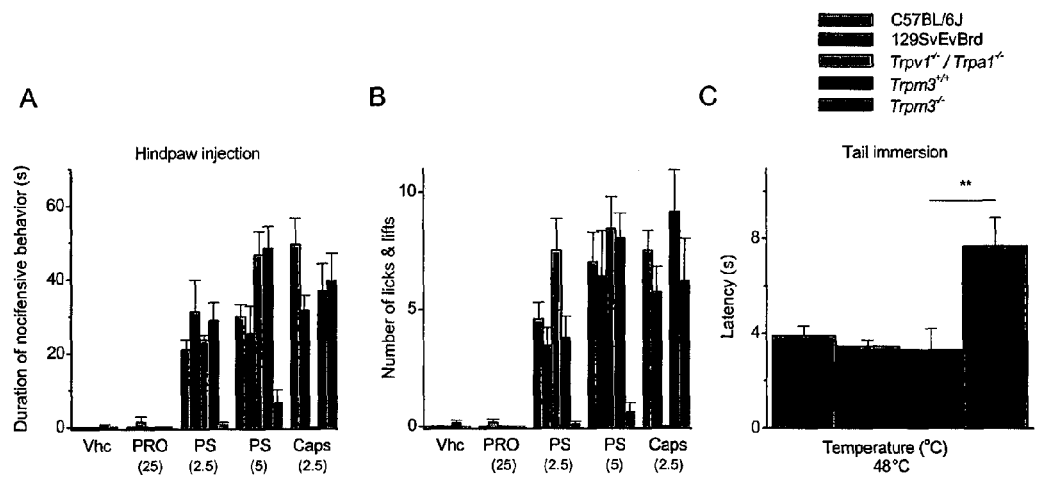

FIG. 13. Behavioral Experiments Performed on Control Strains and Trpm3$^{-/-}$ Mice (A-B) Behavioral responses (paw licks and lifts) to vehicle (Vhc), progesterone (PRO, 25 nmol/hindpaw), pregnenolone sulphate (PS, 2.5 and 5 nmol/hindpaw) and capsaicin (caps, 2.5 nmol/hindpaw) were measured as in FIGS. 4A and 4B for C57BL/6J (n=8), 129SvEvBrd (n=9), Trpv1$^{-/-}$/Trpa1$^{-/-}$ double knockout (n=7), Trpm3$^{+/+}$ and Trpm3$^{-/-}$ mice (n=7).

(C) Response latencies for C57BU6J, 129SvEvBrd, Trpm3$^{+/+}$ and Trpm3$^{-/-}$ mice in tail immersion at 48° C. (n≥7 for each genotype), showing impaired behavioral responses to noxious heat. **, P<0.01, (two sample t-test). Data are represented as mean±SEM.

Figure 14:
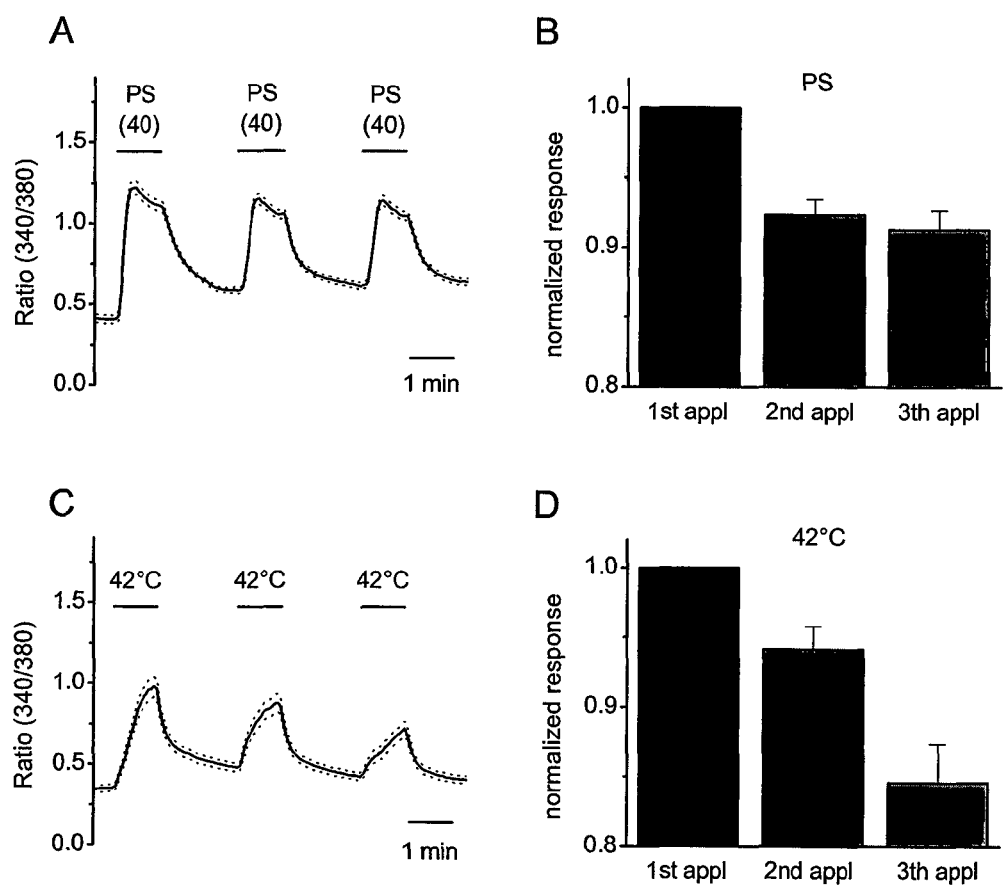

FIG. 14. Modest Desensitization of TRPM3 Responses after Repetitive Activation.

(A and C) $Ca^{2+}$ imaging data for repetitive activation of TRPM3 with 40 μM PS (A) and heat (42° C.) stimuli (C) in TRPM3 stable cell line. (B and D) TRPM3 responses to PS (B) and heat stimuli (42° C.) (D) normalized to the first response. Error bars represent mean±SEM.

Figure 15:
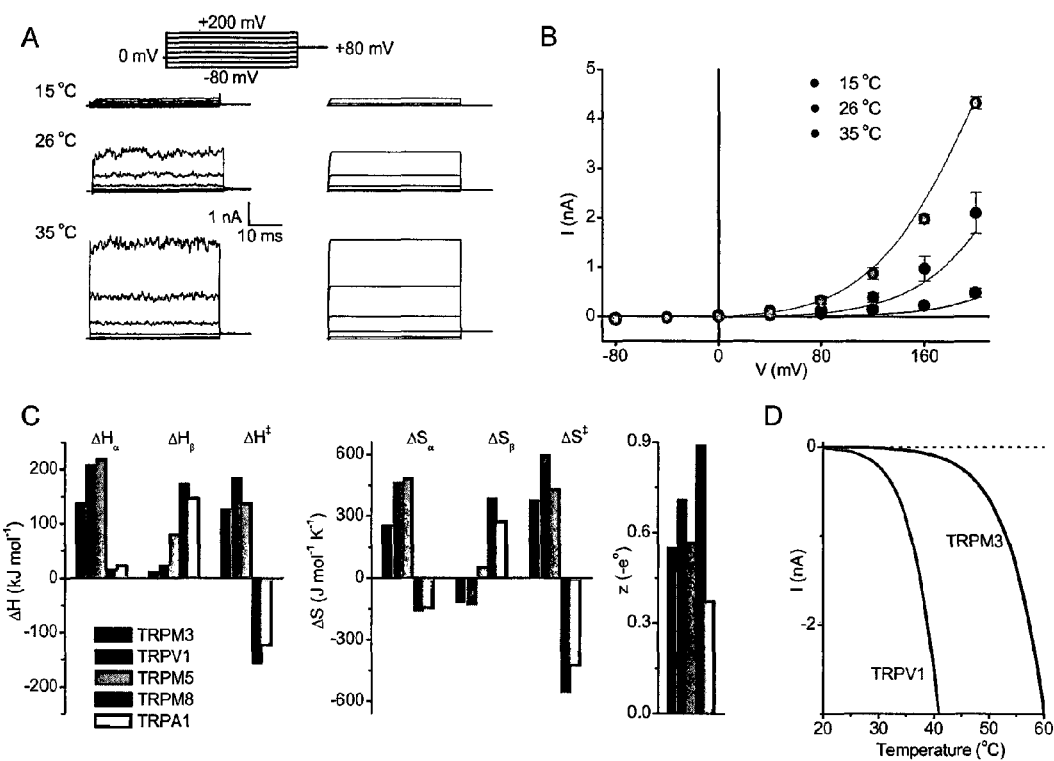

FIG. 15. Modeling TRPM3 as a Thermosensitive Channel (A) Current traces elicited at different temperatures in response to the indicated voltage protocol (left). Simulated current traces at different temperatures as predicted by the two-state model for temperature sensitive TRP channels (right).

(B) Measured average current-voltage traces at different temperatures (closed circles) and fitted traces (line) calculated by the two state model.

(C) Enthalpies and entropies associated with the opening ($\Delta H_\alpha$ and $\Delta S_\alpha$) and closing ($\Delta H_\beta$ and $\Delta S_\beta$) transitions and differences in enthalpy and entropy between the open and closed states ($\Delta H\ddagger$ and $\Delta S\ddagger$), as well as the effective valence of the gating charge (z) for different thermoTRPs.

(D) Comparison of simulated inward TRPV1 and TRPM3 currents at −80 mV in function of temperature, using the parameters shown in (C) and assuming 1000 channels/cell.

Figure 16:
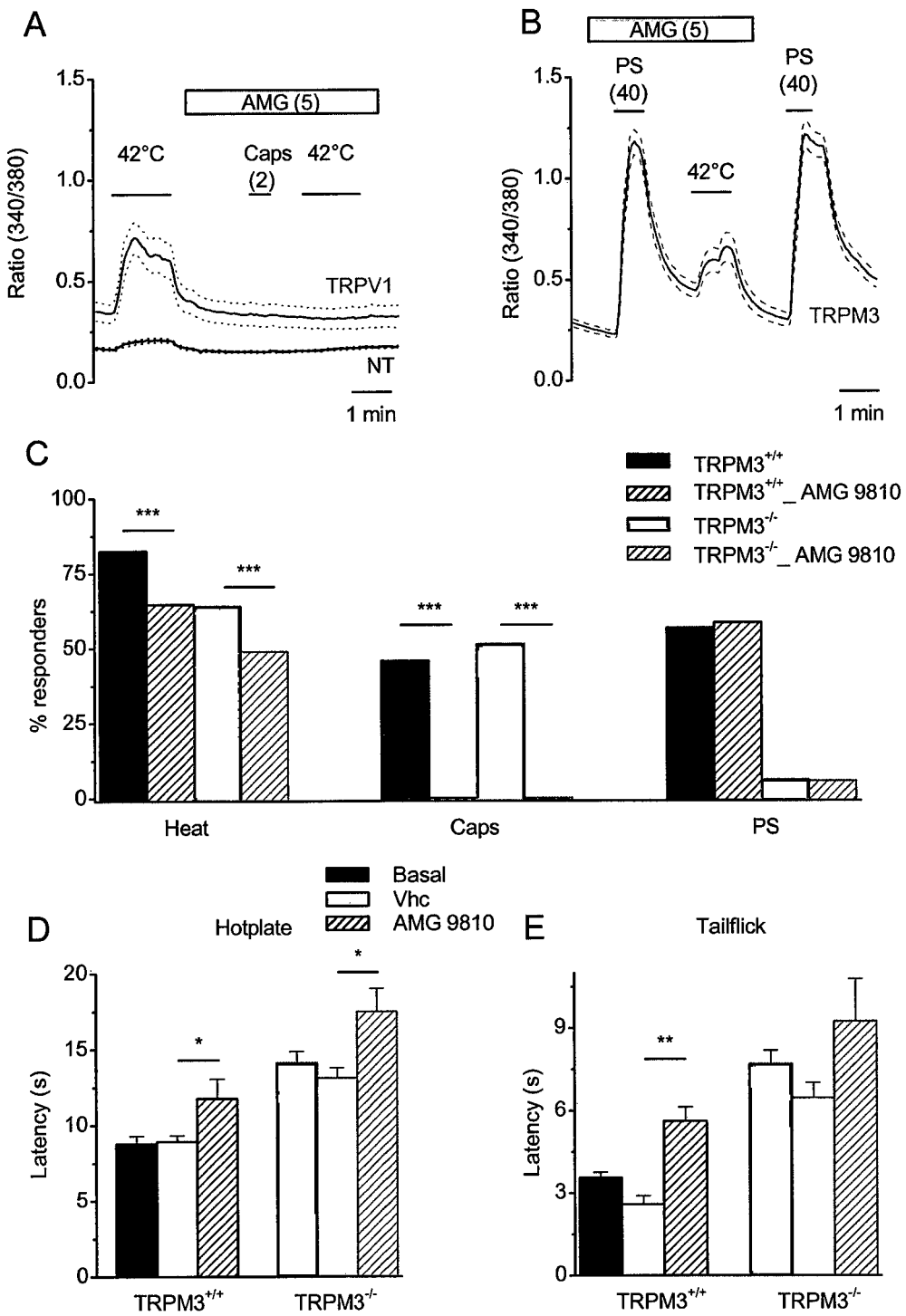

FIG. 16. Heat sensitivity of DRG neurons and nociceptive behavior in the presence of the TRPV1 blocker AMG 9810.

(A-B) $Ca^{2+}$ imaging data showing full inhibition of TRPV1-mediated heat (42° C.) and capsaicin (2 μM) responses (A), but unaltered TRPM3-mediated heat (42° C.) and PS (40 μM) responses (B).

(C) Effect of AMG 9810 (5 μM) on the percentage of DRG neurons from $Trpm3^{+/+}$ and $Trpm3^{-/-}$ mice responding to heat (42° C.) capsaicin (2 μM) and PS (10 μM). ***, $P<0.001$ (Fisher's exact test).

(D-E) Response latencies of $Trpm3^{+/+}$ and $Trpm3^{-/-}$ littermates in hotplate (55° C., D) and tail immersion (48° C.; E) assays (n=6 for each condition), before (basal) and after seven daily injections with vehicle (vhc) or AMG 9810 (3 mg/kg). *, $P<0.05$, **$P<0.01$ (two sample t-test). Data are represented as mean±SEM.

Figure 17:
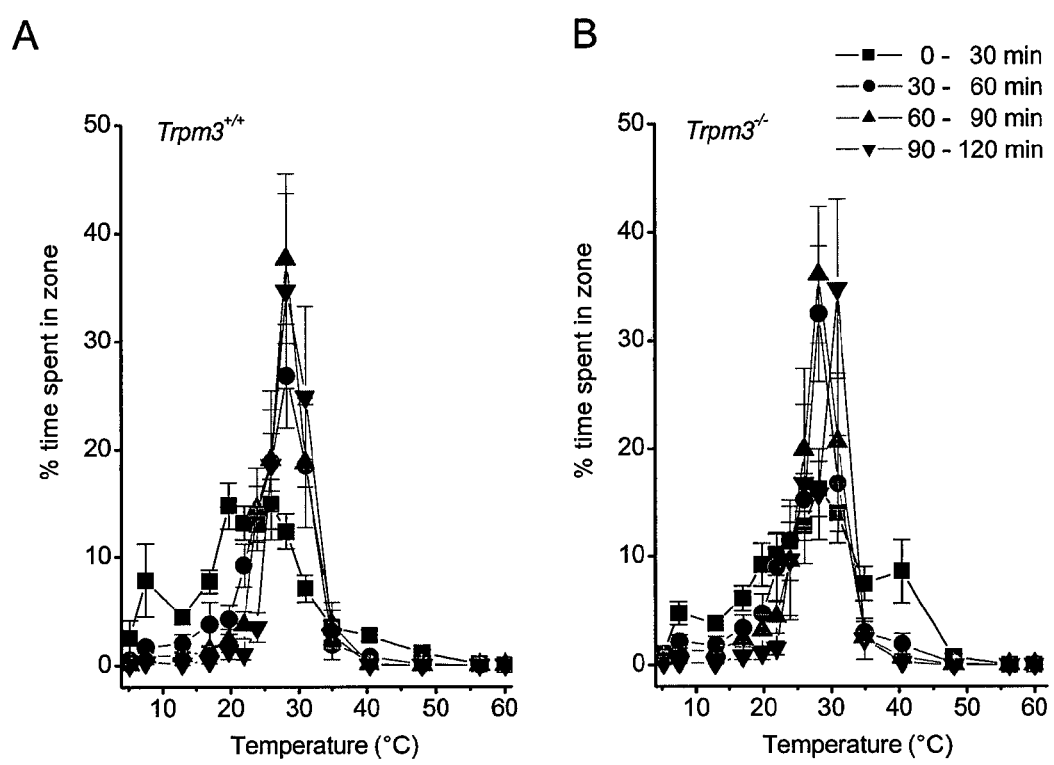

FIG. 17. Thermal Gradient Test (A-B) Behavior of $Trpm3^{+/+}$ (A) and $Trpm3^{-/-}$ (B) mice on the thermal gradient assay over a 2-hour trial, shown in 30-min intervals (n=13 for $Trpm3^{+/+}$ and n=12 for $Trpm3^{-/-}$ mice). Data are represented as mean±SEM.

Figure 18:
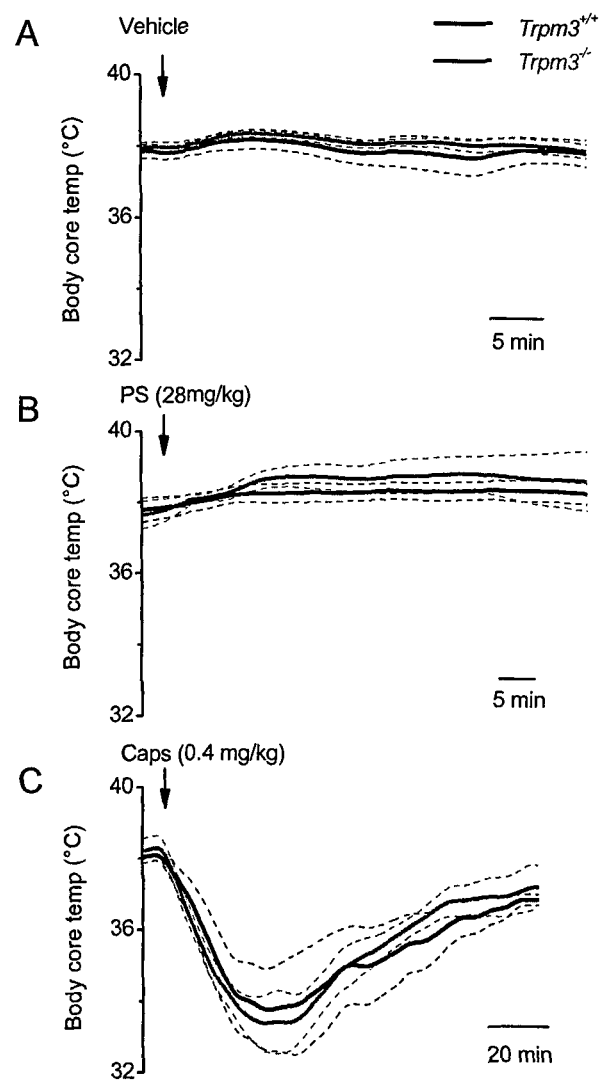

FIG. 18. Body Core Temperature after Injections of PS and Capsaicin (A-C) Body core temperature was measured using the PhysioTel™ telemetry system (DSI International, USA) after subcutaneous injection of vehicle (A), pregnenolone sulphate (PS, 28 mg/kg) (B) and capsaicin (caps, 0.4 mg/kg) (C) in $TRPM3^{+/+}$ (black line) and $TRPM3^{-/-}$ mice (gray line) (n=3 for each genotype, traces represent mean±SEM).

DESCRIPTION

The present invention is based on the surprising finding that TRPM3, a $Ca^{2+}$-permeable non-selective cation channel, is associated with the detection of pain. The detection or sensation of pain is at least in part due to signalling via TRPM3. We have shown that inhibiting TRPM3 function, can be used as analgesics in the treatment and/or prophylaxis of pain and thermal hyperalgesia. Therefore, in a first object the present invention provides the use of TRPM3 antagonists in the manufacture of a medicine for the treatment and/or prophylaxis of pain. When used herein, the term pain relates to all kinds of pain and sensation or perception of pain, diseases or conditions associated with pain. Such pain or diseases or conditions associated with pain are for example, but not limited to, acute pain, chronic pain, neuropathic pain, post-operative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder such as asthma or chronic obstructive pulmonary disease, irritation of skin, eye or mucous membrane, fevescence, stomach-duodenal ulcer, inflammatory bowel disease, hyperalgesia and inflammatory diseases.

In certain embodiments, the invention contemplates agents comprising antagonists or modulators (increase or more particularly decrease) of the activity of TRPM3 and their use, more in particular as a pain decreasing therapeutic or for the manufacture of a medicament for the prevention, treatment or prophylaxis of pain. In other embodiments, the agents of the present invention are selected from small molecules, oligonucleotides (antisense or aptamers), antigene therapeutics, small interfering RNAs (or RNA interference in general), soluble receptors, antibodies and/or cellular therapies.

In the present invention small molecules, e.g. small organic molecules with a molecular mass <500 Da and other suitable molecules, can also function as antagonists or modulators of TRPM3 in order to prevent or treat conditions associated with pain. Small molecules and other drug candidates can readily be obtained, for example, from combinatorial and natural product libraries and using methods known to the art, or screening methods from this invention to screen candidate molecules for their TRPM3 antagonizing or modulating function. Furthermore, random peptide libraries, consisting of all possible combinations of amino acids, attached to a solid phase or in solution, may also be used to identify peptides that act as antagonists of TRPM3.

Suitable antagonists or modulators of TRPM3 can also be developed by known drug design methods, e.g. using structural analysis of known TRPM3 interactors, including inhibitors or antagonists of TRPM3, or the complex of TRPM3 with these interactors by employing methods established in the art, for example, using X-ray crystallography to analyze the structure of the complex formed (see for example Sielecki, A. R. et al. Science 1989; 243:1346-51; Dhanaraj, V. et al. Nature 1992; 357(6377):466-72) and/or by modifying known TRPM3 interactors, more particular inhibitors or antagonists of TRPM3, i.e. "lead compounds," to obtain (more potent) inhibitors and compounds for different modes of administration (i.e. oral vs. intravenous).

The present invention relates to antibodies directed against TRPM3, and disrupting or modulating the complex formation between TRPM3 and compounds, eg. ligands, that interact with TRPM3 and/or stimulate TRPM3, and the use of said antibodies. The invention also relates to the development of antibodies against TRPM3 proteins and to compositions containing them, including naturally raised and recombinantly prepared antibodies. Such antibodies could include both polyclonal and monoclonal antibodies prepared by known genetic techniques, as well as bi-specific (chimeric) antibodies, and antibodies including other functionality suiting them for additional diagnostic use conjunctive with their capability of modulating, in particular inhibiting or antagonizing TRPM3 activity.

Also, antibodies including both polyclonal and monoclonal antibodies, and drugs that modulate the production or activity of TRPM3 and/or their subunits may possess certain diagnostic applications and may for example, be utilized for the purpose of detecting and/or measuring conditions such the sensation of pain or the like.

For example, TRPM3 or fragments thereof may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the agents of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also, U.S. Pat. Nos. 4,341,761; 4,399,121; 4,427,783; 4,444,887; 4,451,570; 4,466,917; 4,472,500; 4,491,632; 4,493,890. Methods for producing monoclonal TRPM3 antibodies are also well-known in the art. See Niman et al., Proc. Natl. Acad. Sci. USA, 80:4949-4953 (1983). Typically, the present TRPM3 or a peptide analog is used either alone or conjugated to an immunogenic carrier, as the immunogen in the before described procedure for producing TRPM3 monoclonal antibodies. The hybridomas are screened for the ability to produce an antibody that immunoreacts with the TRPM3 peptide analog and the present TRPM3.

Panels of monoclonal antibodies produced against TRPM3 peptides can be screened for various properties; i.e., isotope, epitope, affinity, etc. Of particular interest are monoclonal antibodies that neutralize or inhibit or antagonize the activity of TRPM3. Such monoclonals can be readily identified in TRPM3 activity assays. High affinity antibodies are also useful when immunoaffinity purification of native or recombinant TRPM3 is possible.

Methods for producing polyclonal anti-polypeptide antibodies are well-known in the art. See U.S. Pat. No. 4,493,795 to Nestor et al. A monoclonal antibody, typically containing Fab and/or F(ab').sub.2 portions of useful antibody molecules, can be prepared using the hybridoma technology described in Antibodies—A Laboratory Manual, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a TRPM3 protein, or fragment thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present TRPM3 and their ability to inhibit specified TRPM3 activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., Virol. 8:396 (1959)) supplemented with 4.5 gm/l glucose, 20 mm glutamine, and 20% fetal calf serum. An exemplary inbred mouse strain is the Balb/c.

Inhibition of expression of TRPM3 can be desirable to treat or prevent conditions associated with pain. Where inhibition of expression of TRPM3 is desirable, inhibitory nucleic acid sequences that interfere with expression of TRPM3 at the transcriptional or translational level can also be used. The strategy called antisense, antigene or RNA-interference can be applied. These approaches utilise, for example, antisense nucleic acids, ribozymes, triplex agents or siRNAs to block transcription or translation of TRPM3 mRNA or DNA or of a specific mRNA or DNA of TRPM3, either by masking that mRNA with an antisense nucleic acid or DNA with a triplex agent, by cleaving the nucleotide sequence with a ribozyme or by destruction of the mRNA through a complex mechanism involved in RNA-interference.

The present invention extends to antisense oligonucleotides, ribozymes, RNA interference and antigene therapeutics, their use and their preparation.

Antisense nucleic acids are DNA or RNA molecules or nucleic acid analogs (e.g. hexitol nucleic acids, Peptide nucleic acids) that are complementary to at least a portion of a specific mRNA molecule (Weintraub Scientific American 1990; 262:40). In the cell, the antisense nucleic acids hybridise to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesised and are less likely to cause problems than larger molecules when introduced into the target cell which produces TRPM3. Also nucleic acids or analogs, complementary to the translation initiation site, e.g. between 10 or +10 regions of the TRPM3 nucleotide sequence, are preferred.

The potency of antisense oligonucleotides for inhibiting TRPM3 may be enhanced using various methods including addition of polylysine, encapsulation into liposomes (antibody targeted, cationic acid, Sendai virus derived, etc.) or into nanoparticles in order to deliver the oligonucleotides into cells. Other techniques for enhancing the antisense capacity of oligonucleotides exist, such as the conjugation of the antisense oligonucleotides for example to "cell penetrating peptides" (Manoharan, M. Antisense Nucleic Acid Drug Dev. 2002; 12(2): 103-128/Juliano, R.-L. Curr. Opin. Mol. Ther. 2000; 2(3): 297-303).

Use of for example an oligonucleotide or a PNA (Peptide nucleic acid) to stall transcription is known as the antigene strategy (e.g. triplex formation) In the case of oligonucleotides, the oligomer winds around double-helical DNA (major groove), forming a three-stranded helix. Therefore, these antigene compounds can be designed to recognise a unique site on a chosen gene and block transcription of that gene in vivo. (Maher et al. Antisense Res. and Dev. 1991; 1:227; Helene, C. Anticancer Drug Design 1991; 6:569/Casey, B. P. et al. Prog. Nucleic Acid Res. Mol. Biol. 2001; 67: 163-192/ Pooga, M. et al. Biomol. Eng. 2001; 17(6): 183-192/Nielsen, P. E. Pharmacol. Toxicol. 2000; 86(1): 3-7). Antigene oligonucleotides as well as PNAs are easily synthesised by the man skilled in the art and are even commercially available.

Ribozymes are molecules possessing the ability to specifically cleave other single stranded RNA in a manner analogous to DNA restriction endonucleases. Through the modification of nucleotide sequences which encode these RNAs, it is possible to engineer molecules that recognise specific nucleotide sequences in an RNA molecule and cleave it (Cech J. Amer. Med. Assn. 1988; 260:3030). A major advantage of this approach is that, because they are sequence-specific, only mRNAs with particular sequences are inactivated.

There are two basic types of ribozymes namely, tetrahymena-type (Hasselhoff (1988) Nature 334:585) and "hammerhead"-type. Tetrahymena-type ribozymes recognise sequences which are four bases in length, while "hammerhead"-type ribozymes recognise base sequences 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

RNA-interference involves the insertion of small pieces of double stranded (ds) and even single stranded RNA into a cell. If the dsRNA corresponds with a gene in the cell, it will promote the destruction of mRNA produced by that gene, thereby preventing its expression. The technique has been shown to work on a variety of genes, even in human cells and in vivo. For example small interfering RNAs (siRNA), short-hairpin RNAs (shRNA) or vectors expressing such nucleic acids can be applied in the RNA-interference strategy in order to inhibit the translation of TRPM3-mRNA.

Therefore, the present invention relates to the use of nucleic acids mediating RNA interference specific for mRNA of a TRPM3 protein and to the use of nucleic acids mediating RNA interference specific for mRNA of a TRPM3 protein, for the manufacture of a medicament for the prevention and/or treatment of conditions associated with pain. This includes the use of siRNA, shRNA and vectors expressing nucleic acids for RNA interference.

Antisense RNA, DNA molecules and analogs, ribozymes, antigene compounds or nucleic acids for RNA interference of the invention may be prepared by any method known in the art for the synthesis of nucleic acid molecules. These include techniques for chemically synthesizing oligonucleotides well known in the art such as for example solid phase phosphoramidite chemical synthesis. Alternatively, RNA molecules may be generated by in vitro and in vivo transcription of DNA sequences encoding the antisense RNA molecule. The DNA sequences described herein may thus be used to prepare such molecules. Such DNA sequences may be incorporated into a wide variety of vectors which incorporate suitable RNA polymerase promoters such as the T7 or SP6 polymerase promoters. Alternatively, antisense cDNA constructs that synthesize anti-sense RNA constitutively or inducibly, depending on the promoter used, can be introduced stably into cell lines.

Suppression function of TRPM3 can also be achieved through administration of variant polypeptide (dominant negative variant form or soluble receptor) of TRPM3, or a nucleotide sequence encoding variant polypeptide of TRPM3. By administering a TRPM3 variant polypeptide or a nucleotide sequence encoding such polypeptide, the variant will compete with wild-type TRPM3 for transducing its signal and/or form non-functional heterotetrameric TRPM3 channels.

Another aspect of the present invention is the use of gene transfer, including gene therapy, to deliver above mentioned molecules antagonising or modulating the activity of TRPM3. Gene therapy means the treatment by the delivery of therapeutic nucleic acids to patient's cells. This is extensively reviewed in Lever and Goodfellow 1995; Br. Med Bull., 51, 1-242; Culver 1995; Ledley, F. D. 1995. Hum. Gene Ther. 6, 1129. By gene transfer, a nucleic acid encoding a TRPM3-antagonising agent is introduced into cells in a subject to express the TRPM3-antagonist and inhibit the TRPM3 function. To achieve gene therapy there must be a method of delivering genes to the patient's cells and additional methods to ensure the effective production of any therapeutic genes. There are two general approaches to achieve gene delivery; these are non-viral delivery and virus-mediated gene delivery. Vectors as described herein could be used for this purpose. In one embodiment of the invention, nucleic acid encoding an antagonist or modulator of TRPM3 is introduced in a subject in order to express the antagonist or modulator and prevent or treat a condition associated with pain. For gene transfer, the key steps are 1) to select the mode of delivery, e.g. a proper vector for delivery of the inhibitor genes to the subject, 2) administer the nucleic acid to the subject; and 3) achieve appropriate expression of the transferred gene for satisfactory durations. Methods for gene transfer are known in the art. The methods for gene therapy as described herein are merely for purposes of illustration and are typical of those that can be used to practice the invention.

However, other procedures may also be employed, as is understood in the art. Most of the techniques to construct delivery vehicles such as vectors and the like are widely practiced in the art, and most practitioners are familiar with the standard resource materials which describe specific conditions, reagents and procedures which are described in the literature.

In a specific embodiment of the invention, it is clear that the preventive or treatment methods or that the antagonists or modulators of TRPM3 as described herein, can also be used in combination with any therapy or compound known in the art, e.g. for conditions associated with pain. The invention also relates to synergistic combinations, especially combinations with known inhibitors or agents for the treatment of pain.

Another aspect of the present invention relates to a method or a screening method for the identification of an agent for the treatment and/or prophylaxis of pain, wherein said method comprises screening for agents capable of inhibiting TRPM3 function. In certain embodiments of this invention, said inhibiting TRPM3 includes inhibiting or antagonizing the activity of TRPM3 and in other particular embodiments of this invention, said inhibiting TRPM3 includes inhibiting expression of the gene encoding TRPM3.

In further particular embodiments of this invention, said method comprises the steps of:
(a) Loading TRPM3-expressing cells with a labeled compound, e.g. a fluorescent compound, capable of monitoring TRPM3 activity, including but not limited to $Ca^{2+}$-sensitive dyes such as Fura-2, Fluo-4 or related compounds;
(b) Incubating a first group of said loaded TRPM3-expressing cells from step (a) with candidate TRPM3 antagonists, and incubate a second group of said loaded TRPM3-expressing cells from step (a) with vehicle, not containing the candidate TRPM3 antagonist (non-treated cells);
(c) Stimulating TRPM3 activity with a suitable stimulus, such as pregnenolone sulphate, nifedipine or heat; and
(d) Comparing the fluorescent signal between cells incubated with candidate TRPM3 antagonists and non-treated cells (ie. the second group of cells of step, the cells that are not treated with a candidate antagonist). Said comparison can be performed using equipment such as fluorescent microscopes, fluorescent plate readers or microfluorimeters.
A decrease of the fluorescent signal in the first group of cells (the candidate TRPM3 antagonist-treated cells) compared to the second group of cells (the untreated cells) indicate the agent as a TRPM3 antagonist. In certain embodiments, said decrease should be at least a two-fold decrease.

In further particular embodiments of this invention, said method comprises the steps of:
(a) Loading isolated sensory neurons from mouse or rats with a labeled compound, e.g. a fluorescent compound, capable of monitoring TRPM3 activity, including but not limited to Ca2+-sensitive dyes such as Fura-2, Fluo-4 or related compounds;

(b) Incubating a first group of said loaded sensory neurons from step (a) with candidate TRPM3 antagonists, and incubate a second group of said loaded TRPM3-expressing cells from step (a) with vehicle, not containing the candidate TRPM3 antagonist (non-treated cells);

(c) Stimulating TRPM3 activity with a suitable stimulus, such as pregnenolone sulphate, nifedipine or heat; and (d) Comparing the fluorescent signal between sensory neurons incubated with candidate TRPM3 antagonists and non-treated cells (ie. the second group of cells of step, the cells that are not treated with a candidate antagonist). Said comparison can be performed using equipment such as fluorescent microscopes, fluorescent plate readers or microfluorimeters.

A decrease of the fluorescent signal in the first group of cells (the candidate TRPM3 antagonist-treated cells) compared to the second group of cells (the untreated cells) indicate the agent as a TRPM3 antagonist. In certain embodiments, said decrease should be at least a two-fold decrease In further particular embodiments of this invention, said method comprises the steps of:

(a) Whole-cell patch-clamp recordings on TRPM3-expressing cells, wherein whole-cell currents are measured (1) under basal conditions, (2) after stimulation with a TRPM3-activating stimulus such as pregnenolone sulphate, nifedipine or heat, (3) and after addition of candidate TRPM3 antagonists in a first group, or vehicle in a second group, both groups in the continued presence of said activating stimulus; and (b) Comparison of the remaining whole-cell current between cells treated with the candidate TRPM3 antagonist and cells treated with vehicle (untreated cells).

A decrease of the whole-cell current in the first group of cells (the candidate TRPM3 antagonist treated cells) compared to the second group of cells (the untreated cells) indicate the agent as a TRPM3 antagonist. In certain embodiments, said decrease should be at least a two-fold decrease.

In further particular embodiments of this invention, said method comprises the steps of:

(a) Application of candidate TRPM3-antagonists to a first group of laboratory animals and a vehicle treated second group of laboratory animals (untreated group). Said labaratory animals include, but are not limited to mice and rats. Said application include but is not limited to oral application, intraperitoneal injection, intravascular injection, local injection or topical applications;

(b) Local injection (into the intraplantar skin) of a suitable TRPM3 agonist, such as pregnenolone sulphate; and (c) Comparison of the nociceptive response to agonist injection, by monitoring nocifensive behaviour such as licking, lifting, flinching and biting, between animals treated with candidate TRPM3-antagonist and animals treated with vehicle (untreated group).

A decrease of the nociceptive response in the first group, the candidate TRPM3 antagonist treated laboratory animals compared to the second group of vehicle treated laboratory animals (the untreated group) indicate the agent as a TRPM3 antagonist.

In further particular embodiments of this invention, said method comprises the steps of:

(a) Application of candidate TRPM3-antagonists to a first group of laboratory animals and a vehicle treated (application of vehicle only) second group of laboratory animals (untreated group). Said labaratory animals include, but are not limited to mice and rats. Said application include but is not limited to oral application, intraperitoneal injection, intravascular injection, local injection or topical applications; and (b) Comparison of the nociceptive response to a heat stimulus, for example by measuring the withdrawal latency when placed on a hot plate or when the tail is immersed in hot fluid between animals treated with candidate TRPM3-antagonist and animals treated with vehicle (untreated group).

A decrease of the nociceptive response in the first group, the candidate TRPM3 antagonist treated laboratory animals compared to the second group of vehicle treated laboratory animals (the untreated group) indicate the agent as a TRPM3 antagonist.

In further particular embodiments of this invention, said method comprises the steps of:

(a) Measurement of the nociceptive response in laboratory animals to a heat stimulus, for example by measuring the withdrawal latency when placed on a hot plate or when the tail is immersed in hot fluid. Said labaratory animals include, but are not limited to mice and rats;

(b) Induction of local inflammation in said labaratory animals by treatment with a proinflammatory preparation, such as injection of complete freunds adjuvants or topical application of mustard oil;

(c) Application of candidate TRPM3-antagonists to said laboratory animals of step (b). Said application include but is not limited to oral application, intraperitoneal injection, intravascular injection, local injection or topical applications;

(d) Measurement of the nociceptive response of the candidate TRPM-3 antagonist treated laboratory animals of step (c) to a heat stimulus, for example by measuring the withdrawal latency when placed on a hot plate or when the tail is immersed in hot fluid; and (e) Comparison of the nociceptive response in the second heat-treated animals of step (d), with the nociceptive response to the first heat-treated animals of step (a). A decrease or status quo of the nociceptive response in the second heat treated group of step (d) compared to the first heat treated group of step (a), indicate the agent as a TRPM3 antagonist. Such agent can be used as analgesics in the treatment and/or prophylaxis of pain and hyperalgesie, including thermal hyperalgesie and more in particular inflammatory hyperalgesia.

When used herein, the term TRPM3 relates to the Transient Receptor Potential Melastatin-3 including all isoforms of TRPM3. Isoforms exist due to alternative splicing and exon usage.

Certain receptor antagonists may exist in one of several tautomeric forms, all of which are encompassed by the present invention as individual tautomeric forms or as mixtures thereof. Where a TRPM3 antagonist contains a chiral carbon, and hence exists in one or more stereoisomeric forms or where one or more geometric isomers exist, it will be appreciated that the method of the present invention encompasses all of the said forms of the TRPM3 antagonists whether as individual isomers or as mixtures of isomers, including racemates. When used herein the term 'TRPM3 antagonist' relates to an antagonist, such as a small molecular weight antagonist, of the Transient Receptor Potential Melastatin-3 including all isoforms of TRPM3. It will be appreciated that the term also embraces suitable pharmaceutically acceptable derivatives thereof. Suitable pharmaceutically acceptable derivatives of a TRPM3 antagonist are, for example, salts and solvates. Suitable pharmaceutically acceptable salts include salts derived from appropriate acids, such as acid addition salts, or bases.

A "vector" is a replicon, such as plasmid, phage or cosmid, to which another DNA segment may be attached so as to bring about the replication of the attached segment.

A "replicon" is any genetic element (e.g., plasmid, chromosome, virus) that functions as an autonomous unit of DNA replication in vivo; i.e., capable of replication under its own control.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alis, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

The term "oligonucleotide," as used herein in referring to the probe of the present invention, is defined as a molecule comprised of two or more (deoxy)ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers or oligonucleotides herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

A "cell line" is a clone of a primary cell that is capable of stable growth in vitro for many generations.

A "clone" is a population of cells derived from a single cell or common ancestor by mitosis. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab').sub.2 and F(v), which portions are preferred for use in the therapeutic methods described herein.

Fab and F(ab').sub.2 portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab') portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

As used herein the term 'pharmaceutically acceptable' embraces compounds, compositions and ingredients for both human and veterinary use: for example the term 'pharmaceutically acceptable salt' embraces a veterinary acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged, for instance a pharmaceutical composition, which can be topically applied on the zone of the body where the pain is occurring.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate, sodium lauryl sulphate or sucrose.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Compositions may contain from 0.1% to 99% by weight, preferably from 10-60% by weight, of the active material, depending upon the method of administration. Compositions may, if desired, be in the form of a pack accompanied by written or printed instructions for use.

The compositions are formulated according to conventional methods, such as those disclosed in standard reference texts, for example the British and US Pharmacopoeias, Remington's Pharmaceutical Sciences (Mack Publishing Co.), Martindale The Extra Pharmacopoeia (London, The Pharmaceutical Press) and Harry's Cosmeticology (Leonard Hill Books).

All publications, including but not limited to patents and patent applications, cited in this specification are herein incorporated by reference as if each individual publication were specifically and individually indicated to be incorporated by reference herein as though fully set forth.

The invention is further illustrated by way of the illustrative embodiments described below.

TRPM3 is Molecularly and Functionally Expressed in Somatosensory Neurons

Using quantitative real time-PCR on freshly isolated mouse DRG and TG, we detected TRPM3 mRNA at levels comparable to that of known somatosensory TRP channels TRPA1, TRPM8, TRPV1, and TRPV2, and higher than that of the heat-activated TRPV3 and TRPV4 (FIG. 1A). These results are in line with earlier studies showing significant TRPM3 mRNA levels in sensory neurons (Lechner et al., 2009; Nealen et al., 2003; Staaf et al., 2010). In situ hybridization using a TRPM3-specific antisense RNA probe yielded a strong signal in the cell bodies of a large fraction of DRG and TG neurons, comparable to the signals obtained with a TRPV1-specific antisense RNA probe (FIG. 1B and FIG. 9). Visual inspection of different sections revealed a positive TRPM3 hybridization signal in 78±6% of DRG neurons and 82±5% TG neurons. Taken together, these data indicate the abundant presence of TRPM3 mRNA in sensory neurons.

To examine functional expression and in vivo function of TRPM3 in the somatosensory system, we made use of a functionally uncharacterized TRPM3-deficient mouse strain (FIG. 10). Western blot analysis demonstrated TRPM3 protein expression in DRG and TG tissue from Trpm3$^{+/+}$ but not from Trpm3$^{-/-}$ mice (FIG. 1C). Trpm3$^{-/-}$ mice were viable, fertile, and exhibited no obvious differences from Trpm3$^{+/+}$ controls in terms of general appearance, gross anatomy, body weight (at 10 weeks: 24.9 g±0.9 in Trpm3$^{+/+}$ and 27.0 g±0.9 in Trpm3$^{-/-}$ mice (n=15 for each group; P=0.29)), core body temperature (37.89±0.1° C. in Trpm3$^{+/+}$ and 38.06±0.2° C. in Trpm3$^{-/-}$ mice (n=6 for each group; P=0.45)), heart rate (629±25 bpm in Trpm3$^{+/+}$ and 585±29 bpm in Trpm3$^{-/-}$ mice (n=6; P=0.28)) and basal blood glucose levels (135±4 mg/dl in Trpm3$^{+/+}$ and 135±4 mg/dl in Trpm3$^{-/-}$ mice (n=7; P=0.96)).

Previous work revealed that the mouse TRPM3α2 isoform is rapidly and reversibly activated by low micromolar concentrations of the neurosteroid PS, and that PS is not acting on several other TRP channels expressed in DRG or TG neurons, including TRPV1, TRPV2, TRPA1 or TRPM8 (FIG. 4A and data not shown) (see also Chen and Wu, 2004; Wagner et al., 2008). We therefore used PS to test for functional TRPM3 expression in freshly isolated DRG and TG neurons. PS evoked robust and reversible calcium signals in 58% of DRG (n=303) (FIG. 2A) and 57% of TG neurons (n=273) isolated from Trpm3$^{+/+}$ mice (FIG. 2A, 2C-2D and FIG. 11). PS responses, like capsaicin responses (Caterina et al., 2000; Davis et al., 2000), were restricted to small-diameter cells (diameter <25 µm; FIG. 3), known to include unmyelinated nociceptors neurons. Importantly, the fraction of PS-sensitive neurons was drastically decreased in DRG and TG preparations from Trpm3$^{-/-}$ mice (FIG. 2B-2D and FIG. 11), whereas the fractions that responded to the TRPA1 agonist MO or the TRPV1-agonist capsaicin were not changed (FIGS. 2C and 2D). Conversely, responses to PS were conserved in DRG and TG neurons obtained from Trpv1$^{-/-}$, Trpa1$^{-/-}$ and combined Trpv1$^{-/-}$/Trpa1$^{-/-}$ mice (FIG. 12A-12E). In some experiments, we also stimulated sensory neurons with nifedipine (10 µM), a drug that has been described as an agonist of both TRPA1 (EC50=0.4 µM Fajardo et al., 2008) and TRPM3 (EC50=30 µM Wagner et al., 2008). We found that the fraction of nifedipine-sensitive neurons was not significantly altered in DRG and TG preparations from Trpm3$^{-/-}$ mice, in line with previous work suggesting that TRPA1 is the main determinant of nifedipine-induced Ca$^{2+}$ responses in sensory neurons (Fajardo et al., 2008).

In whole-cell patch-clamp experiments on TG neurons, PS also produced inward currents of more than 10 pA in 65% TG neurons (15 of 23) from Trpm3$^{+/+}$ mice and in 53% TG neurons (9 of 17) from Trpv1$^{-/-}$/Trpa1$^{-/-}$ mice, which were never observed in neurons from Trpm3$^{-/-}$ mice (0 of 21; P<0.001) (FIG. 2E-2G). TRPM3-deficient neurons exhibited unaltered responses to capsaicin (FIG. 2F insert): 57% of Trpm3$^{+/+}$ TG neurons responded to capsaicin (13 of 23) compared to 53% responders in Trpm3$^{-/-}$ TG neurons (11 of 21). PS-induced currents recorded in Trpm3$^{+/+}$ DRG neurons in the absence of extracellular monovalent cations exhibited an outwardly rectifying current-voltage relationship with a reversal potential close to 0 mV (FIG. 2H-2J), in agreement with the characteristics of heterologously expressed TRPM3α2 channels (Oberwinkler et al., 2005; Wagner et al., 2008). Taken together, these data demonstrate that TRPM3 is functionally expressed in a large fraction of DRG and TG neurons, and is the major receptor for PS in these cells.

PS-Induced Activation of TRPM3 Evokes Pain

To directly investigate whether TRPM3 activation can evoke pain, we tested for nocifensive behavior in Trpm3$^{+/+}$ and Trpm3$^{-/-}$ mice following injection of PS into the plantar skin of the hind paw. Injection of vehicle or progesterone (25 nmol/paw), a closely related neurosteroid with no TRPM3 agonist activity (Wagner et al., 2008), did not evoke measurable nociceptive responses in Trpm3$^{+/+}$ or Trpm3$^{-/-}$ mice (FIGS. 4A and 4B). In contrast, injection of PS (2.5 and 5 nmol/paw) evoked strong nocifensive behavior (paw licking and lifting) in Trpm3$^{+/+}$ mice (FIG. 4A, 4B). Importantly, Trpm3$^{-/-}$ mice completely lacked this nocifensive response to PS, whereas injection of the TRPV1-agonist capsaicin evoked the normal nocifensive behavior (Caterina et al., 2000) (FIGS. 4A and 4B). As the Trpm3$^{+/+}$ and Trpm3$^{-/-}$ littermates are in a heterogenously mixed genetic background of 129SvEvBrd and C57BL/6J mouse strains, we envisaged the possibility that the deficits in behavioral PS responses could be attributable to the linkage of other 129SvEvBrd-derived determinants to the disrupted TRPM3 locus. We therefore tested age-matched 129SvEvBrd and C57BL/6J mice for their sensitivity to PS, and found similar behavioral responses as in the Trpm3$^{+/+}$ mice (FIG. 13A, B). Moreover, injection of PS in combined Trpv1$^{-/-}$/Trpa1$^{-/-}$ knockout mice elicited a nocifensive response that was similar to that observed in Trpm3$^{+/+}$ mice (FIG. 13A, B).

To evaluate the contribution of TRPM3 to trigeminal nociception, we used an aversive drinking test (Caterina et al., 2000). Over a period of 3 days, mice were allowed to drink from a bottle of water for only 1 hour/day. On the fourth day, this solution was supplemented with PS (750 µM). In Trpm3$^{+/+}$ mice, this evoked a modest but significant aversion, as evidenced by a 30% reduction in consumed water volume (FIG. 4C). In contrast Trpm3$^{-/-}$ mice showed no aversive response and drank at the previous day's rate (FIG. 4C). Taken together, our results show that TRPM3 is functionally expressed in the somatosensory system and mediates the nociceptive effect of PS.

TRPM3 is Activated by Heat

Whereas these data clearly demonstrate that activation of TRPM3 by exogenous PS can evoke pain, it is unclear whether endogenous PS concentrations in the sensory system can ever reach levels that are sufficient to activate TRPM3 in vivo (Nilius and Voets, 2008; Wagner et al., 2008). We therefore hypothesized that other physiologically relevant stimuli may cause pain through activation of TRPM3. Given that several closely related TRPM channels (TRPM8, TRPM4, TRPM5 and TRPM2) are thermosensitive (McKemy et al., 2002; Peier et al., 2002a; Talayera et al., 2005; Togashi et al., 2006), we tested for temperature effects on TRPM3.

To test this possibility, we first compared intracellular Ca$^{2+}$ responses to agonist and heat in HEK293T cells transiently expressing TRPM3 or TRPV1. TRPM3-expressing cells exhibited robust responses to PS and heat (40° C.), but were insensitive to capsaicin (FIGS. 5A and 5B). The magnitude of the heat response was similar to that in TRPV1-expressing cells, which also responded to capsaicin but not to PS (FIG. 5B). Repetitive applications of an identical heat stimulus resulted in partly desensitizing responses, similar to what we observed with repetitive PS stimuli (FIG. 14). Thermal sensitivity was confirmed in whole-cell patch-clamp recordings of TRPM3-expressing HEK cells, showing marked and reversible activation of a strongly outwardly rectifying current upon heating (FIG. 5C-5F). From the average temperature-induced increase in inward current at −80 mV (FIG. 5F, inset) we calculated a 10-degree temperature coefficient ($Q_{10}$) value of 7.2.

We have previously shown that thermal activation of other TRP channels, including the cold-activated TRPM8 and TRPA1 and the heat-activated TRPV1, TRPM4 and TRPM5, involves a shift of the voltage dependence of channel activation and can be approximated by a two-state model (Karashima et al., 2009; Talayera et al., 2005; Voets et al., 2004). Detailed analysis of whole-cell currents at different voltages and temperatures revealed that thermal activation of TRPM3 can also be described using this two-state formalism (FIG. 15A-C). The derived values for the enthalpy and entropy associated with opening of TRPM3 were ~30% lower than those determined for TRPV1 (FIG. 15C). Following this analysis, the current-temperature relation of inward TRPM3 current at −80 mV is shifted towards higher temperatures compared to TRPV1 (FIG. 15D), and exhibits a lower steepness as reflected in maximal $Q_{10}$ values between 20 and 30° C. of 7.5 for TRPM3 versus 16.8 for TRPV1.

Previous work on other thermosensitive TRP channels has shown synergistic effects between chemical agonists and thermal stimuli. For example, menthol responses of the cold-activated TRPM8 are potentiated at low temperatures, and non-activating proton concentrations sensitize TRPV1 for heat activation (McKemy et al., 2002; Peier et al., 2002a; Tominaga et al., 1998). We observed a similar synergism of heat and PS on TRPM3. Using a 96 well plate-based assay to determine temperature-dependent Ca$^{2+}$-responses (Reubish et al., 2009), we found that PS at 10 µM shifted the thermal response profile of TRPM3-expressing cells to lower temperatures by 6.1±0.4 degrees (FIG. 6A).

Conversely, we found that increasing the temperature from room temperature to 37° C. strongly potentiated PS responses (FIG. 6B,C). Interestingly, PS concentrations as low as 100 nM, which are subthreshold at room temperature, evoked robust responses at 37° C. (FIG. 6B,C). The synergism between heat and PS was further confirmed in whole-cell current measurements, where the current response to a low dose of PS (5 µM) was strongly potentiated at higher temperatures (FIG. 6D-6F). Taken together, these data demonstrate that heterologously expressed TRPM3 functions as a heat-activated channel, capable of integrating chemical and thermal stimuli.

TRPM3 Contributes to Heat Sensitivity in DRG and TG Neurons.

To analyze the possible contribution of TRPM3 to heat sensitivity in DRG and TG neurons, we used Ca$^{2+}$ imaging to probe for heat responses in sensory neurons from Trpm3$^{+/+}$ and Trpm3$^{-/-}$ mice and to correlate heat responsiveness with sensitivity to PS and capsaicin (FIG. 7A). In line with earlier work (Fischbach et al., 2007; Woodbury et al., 2004), we found that the large majority of sensory neurons from Trpm3$^{+/+}$ mice showed heat sensitivity, with 82% of DRG neurons ($^{111}/_{135}$) and 79% of TG neurons ($^{126}/_{159}$) responding to a 43° C. heat stimulus. The heat-sensitive population could be further classified in four groups based on PS and capsaicin sensitivity. The largest fraction of heat-positive Trpm3$^{+/+}$ DRG neurons ($^{59}/_{135}$; 43%) responded to both PS and capsaicin. In addition, 33% of the heat-sensitive neurons responded to PS but not to capsaicin ($^{45}/_{135}$), and 3% responded to capsaicin but not to PS ($^{4}/_{135}$). Finally, 3 out of 135 (2%) were insensitive to both capsaicin and PS (FIG. 7C). The responsiveness to heat was not different when the thermal stimulus was applied prior to the chemical agonists (data not shown). A similar response profile was obtained in Trpm3$^{+/+}$ TG neurons and in TRPV1$^{+/+}$ DRG and TG neurons (FIG. 7D). Sensory neurons from Trpm3$^{-/-}$ mice showed a moderate but significant reduction in the heat sensitivity, with 59% of DRG neurons ($^{129}/_{217}$; P<0.001) and 63% of TG neurons ($^{150}/_{236}$; P<0.001) responding to a 43° C. heat stimulus (FIG. 7B-7D). In particular, the subgroup of heat-sensitive neurons responding to PS but not to capsaicin was strongly reduced in the Trpm3$^{-/-}$ mice (FIG. 7B-7D). For comparison, we also analysed heat, PS and capsaicin sensitivity in neurons isolated from Trpv1$^{-/-}$ mice. Here, we found that 60% of DRG neurons and 62% of TG neurons responded to heat (FIGS. 7C and 7D).

The large majority of heat-sensitive Trpv1$^{-/-}$ neurons also responded to PS (10 μM) application (FIGS. 7C and 7D).

To further dissect the relative contribution of TRPM3 and TRPV1 to heat sensitivity of sensory neurons, we investigated the effect of the selective TRPV1 antagonist AMG 9810; (FIG. 16A,B Gavva et al., 2005) on heat responses in Trpm3$^{+/+}$ and Trpm3$^{-/-}$ DRG neurons. At a concentration of 5 μM, AMG 9810 completely eliminated capsaicin responses and significantly reduced the percentage of heat responders (FIG. 16C). However, we still observed a substantial fraction of heat-responsive cells after treatment of Trpm3$^{-/-}$ neurons with AMG 9810 (FIG. 16C). Taken together, these experiments demonstrate that both TRPV1 and TRPM3 contribute to heat responses in DRG and TG neurons, but also indicate the existence of TRPV1- and TRPM3-independent heat sensing mechanisms in sensory neurons.

Trpm3$^{-/-}$ Mice Exhibit Reduced Sensitivity to Noxious Heat

To investigate whether TRPM3 is involved in heat sensation in vivo, we compared the behaviour of Trpm3$^{+/+}$ and Trpm3$^{-/-}$ mice in different nociceptive and thermosensory assays. In the tail immersion test, Trpm3$^{-/-}$ mice animals exhibited strongly increased tail flick latencies compared to Trpm3$^{+/+}$ littermates for bath temperatures between 45 and 57° C., (FIG. 8A). The delayed response was not a consequence of overall slower reactivity of the mouse-tail, as Trpm3$^{-/-}$ mice exhibited a normal response delay to mechanical stimuli (tail clip assay; FIG. 8C). Trpm3$^{-/-}$ and Trpm3$^{+/+}$ mice were also indistinguishable in their response to intense tail pinching, with response delays <1 s for both genotypes (n=9). In the hot plate assay, Trpm3$^{-/-}$ mice exhibited normal latencies at a plate temperature of 50° C., but responded with a significantly longer delay at temperatures between 52 and 58° C. (FIG. 8B). To exclude a possible interference of the heterogenous genetic background of the Trpm3$^{+/+}$ and Trpm3$^{-/-}$ littermates on the behavioural response to thermal stimuli (Mogil et al., 1999), we repeated the tail immersion assay using age-matched 129SvEvBrd and C57BL/6J mice. The response latencies of mice of both strains were comparable to those of the Trpm3$^{+/+}$ mice, and significantly faster than those of Trpm3$^{-/-}$ mice (FIG. 13C).

We also compared the thermal preference of Trpm3$^{+/+}$ and Trpm3$^{-/-}$ mice when allowed to move freely for 2 hours on a flat rectangular platform with a surface temperature gradient of 5 to 60° C. along the length (Lee et al., 2005; Moqrich et al., 2005). We observed that over the entire duration of the assay Trpm3$^{+/+}$ and Trpm3$^{-/-}$ mice showed a very similar behaviour, and spent most of the time in the temperature zone between 27 and 31° C. (FIG. 8D and FIG. 14). However, when analysing the first 30 minutes, which mainly corresponds to the period of exploration (Moqrich et al., 2005), Trpm3$^{-/-}$ mice spent significantly more time at temperatures between 31 and 45° C. than control animals (FIG. 8E). Both genotypes covered a similar distance on the platform and had a comparable time of inactivity, suggesting that TRPM3 deficiency does not influence exploratory behaviour. These results indicate that Trpm3$^{-/-}$ mice have the same thermal preference as Trpm3$^{+/+}$ animals, but exhibit a reduced avoidance to higher temperatures. This was confirmed in two-plate preference tests (FIG. 8F), where Trpm3$^{-/-}$ mice exhibited a reduced preference for the 30-° C. plate over warmer plates (38 and 45° C.), but unaltered avoidance of the cold temperature (15° C.). Taken together, our data indicate that TRPM3 is specifically required for heat sensation.

To investigate a potential role of TRPM3 in temperature homeostasis, we compared the effect of subcutaneous injections of PS and capsaicin in Trpm3$^{+/+}$ and Trpm3$^{-/-}$ mice (FIG. 18). Capsaicin evoked clear hypothermia in both genotypes, in line with previous work (Caterina et al., 2000). In contrast, PS was without effect on core body temperature, in spite of clear nociceptive behavior in the Trpm3$^{+/+}$ mice.

Finally, we investigated whether TRPM3 may be involved in the involvement of thermal hyperalgesia during inflammation. In line with previous work, we found that injection of complete Freund's adjuvant (CFA) in the hind paw of Trpm3$^{+/+}$ mice results in a strong sensitisation to hot and cold stimuli, as evidenced by a reduced withdrawal latency on the hot plate assay and stronger nocifensive behaviour on the cold plate (FIG. 8G,H). Surprisingly, whereas Trpm3$^{-/-}$ mice developed similar signs of cold hyperalgesia, CFA injection did not alter their hot plate withdrawal latency (FIG. 8G,H). These data indicate that Trpm3$^{-/-}$ mice have a strong deficit in the development of heat hyperalgesia, similar to what has been reported for TRPV1-deficient mice (Caterina et al., 2000; Davis et al., 2000).

The first characterization of Trpv1$^{-/-}$ mice, about one decade ago, not only provided conclusive evidence for the crucial role of TRPV1 in noxious heat detection, thermal hyperalgesia and pain, but also indicated the existence of additional noxious heat sensors in sensory neurons (Caterina et al., 2000; Davis et al., 2000). Since then, the role of different thermosensitive TRP channels in the detection of cold and warm temperatures has been well established. Yet, the molecular basis of TRPV1-independent noxious heat sensing remained fully elusive. In the past, several other heat-activated TRP channels had been identified, but none of them was shown to function as a heat sensor in sensory neurons. Here, we identified TRPM3 as a novel noxious heat sensor expressed in a large subset of small-diameter sensory neurons, and demonstrate that it plays an unanticipated role in noxious heat sensing. Whereas TRPM3 and TRPV1 share only limited sequence homology, our present results reveal a surprising functional similarity: both form heat-activated, calcium-permeable cation channels; both are functionally expressed in a large proportion of small-diameter sensory neurons, both are involved in the nociceptive behavioural responses to chemical ligands and noxious heat, and both are required for the development of heat hyperalgesia following an inflammatory challenge.

Previous work indicated TRPM3 expression, at the mRNA level and/or protein level, in various tissues, including brain, kidney, endocrine pancreas, vascular smooth muscle and sensory neurons (Grimm et al., 2003; Lechner et al., 2009; Lee et al., 2003; Naylor et al., 2010; Nealen et al., 2003; Oberwinkler et al., 2005; Oberwinkler and Philipp, 2007; Staaf et al., 2010; Wagner et al., 2008). Reported in vitro TRPM3-activating stimuli included hypotonic cell swelling, internal Ca$^{2+}$ store depletion, D-erythro-sphingosine and PS (Grimm et al., 2003; Grimm et al., 2005; Lee et al., 2003; Wagner et al., 2008). With the use of PS, which is currently the most potent and selective available pharmacological tool to probe for biological roles of TRPM3 (Wagner et al., 2008), evidence has been provided suggesting functional expression of the channel in pancreatic beta cells and vascular smooth muscle (Naylor et al., 2010; Wagner et al., 2008). However, the actual stimuli that regulate TRPM3 activity in vivo and the physiological roles of TRPM3 remained largely unknown. Here, we provide the first description of Trpm3$^{-/-}$ mice, which will form a firm basis for further investigation of the biological roles of TRPM3. Trpm3$^{-/-}$ mice exhibited no obvious deficits in fertility, gross anatomy, body weight, core body temperature, locomotion or exploratory behaviour. With respect to the proposed role of TRPM3 in insulin release, we also did not find differences in resting blood glucose, suggesting that basal glucose homeostasis is not critically affected. Thus, Trpm3$^{-/-}$ mice appear generally healthy, with no indications of major developmental or metabolic deficits.

In addition, several behavioural aspects related to somatosensation and nociception were unaltered in the Trpm3$^{-/-}$ mice, including the avoidance of cold temperatures and the nocifensive response to mechanical stimuli or capsaicin injections. We found, however, significant and specific deficits in the nocifensive responses to TRPM3-activating stimuli. First, we confirmed and further substantiated an earlier study showing that injection of PS elicits pain in mice (Ueda et al., 2001). Intraplantar injection of PS in Trpm3$^{+/+}$ mice induced a strong nocifensive response, consisting of vigorous licking and lifting of the hind paw, which was comparable to what we observed upon injection of the TRPV1 agonist capsaicin. This pain response was conserved in Trpv1$^{-/-}$/Trpa1$^{-/-}$ double knockout mice but fully abrogated in Trpm3$^{-/-}$ mice, indicating that TRPM3 is the main PS sensor in nociceptors. Similarly, we found that addition of PS to the drinking water led to a moderate reduction of water consumption in Trpm3$^{+/+}$ but not in Trpm3$^{-/-}$ mice, indicative of TRPM3-dependent PS aversion. Second, we found that Trpm3$^{-/-}$ mice exhibit a strong deficit in the detection of noxious heat stimuli, as evidenced by prolonged reaction latencies in the tail immersion and hot plate assays, and a reduced avoidance of hot temperature zones in the thermal gradient and thermal preference tests. The difference in heat responsiveness between Trpm3$^{+/+}$ and Trpm3$^{-/-}$ mice was even more pronounced following injection of CFA. This inflammatory challenge caused a significant reduction in the response latencies of Trpm3$^{+/+}$ mice, indicative of heat hyperalgesia, but did not change the heat response latencies in Trpm3$^{-/-}$ mice. Taken together, these results establish TRPM3 as a chemo- and thermosensor in the somatosensory system, involved in the detection of noxious stimuli in healthy and inflamed tissue.

Our analysis of the heat, capsaicin and PS sensitivity of DRG and TG neurons from Trpm3$^{+/+}$, Trpm3$^{-/-}$, Trpv1$^{+/+}$ and Trpv1$^{-/-}$ mice indicates the existence of at least four distinct subsets of heat-sensitive neurons. The largest subset encompasses heat-sensitive neurons that responded to both PS and capsaicin, suggesting co-expression of TRPV1 and TRPM3. In addition, we identified heat sensitive neurons that responded to capsaicin but not to PS (TRPV1-expressing), or to PS but not to capsaicin (TRPM3-expressing). Finally, a fraction of heat-activated neurons was unresponsive to both PS and capsaicin, indicating the existence of a TRPM3- and TRPV1-independent heat sensing mechanism. In line herewith, we observed a substantial fraction of heat-sensitive cells after pharmacological inhibition of TRPV1 in DRG and TG preparations from Trpm3$^{-/-}$ mice. Moreover, Trpm3$^{-/-}$ mice treated with a selective TRPV1 antagonist still responded to noxious heat, albeit with increased latency. The molecular and cellular mechanisms underlying this residual thermosensitivity are currently unknown.

How does the heat sensitivity of TRPM3 compare to that of TRPV1 and other thermosensitive TRP channels? From the temperature-induced change in inward TRPM3 current, we determined a maximal $Q_{10}$ value of ~7, which is comparable to the $Q_{10}$ values between 6 and 25 that have been reported for other heat-activated TRP channels, including TRPV1-TRPV4, TRPM2 and TRPM5 (Caterina et al., 1999; Caterina et al., 1997; Guler et al., 2002; Peier et al., 2002b; Smith et al., 2002; Talayera et al., 2005; Togashi et al., 2006; Watanabe et al., 2002). Our analysis of the thermodynamic parameters associated with channel gating further indicated that the temperature dependence of TRPM3 activation is shifted to higher temperature compared with TRPV1. It should be noted, however, that the thermal threshold for heat- or cold-induced action potential initiation in a sensory nerve will not only depend on the thermal sensitivity of the depolarizing thermosensitive (TRP) channels, but also on their expression levels at the sensory nerve endings and on the relative amplitude of other conductances, in particular voltage-gated Na$^+$ channels and various K$^+$ conductances (Basbaum et al., 2009; Madrid et al., 2009; Noel et al., 2009; Viana et al., 2002). In addition, the thermal sensitivities of TRP channels are known to be modulated by various intra- and extracellular factors (Basbaum et al., 2009; Damann et al., 2008). In this respect, we found a prominent enhancement of the heat sensitivity of TRPM3 by the neurosteroid PS. In particular, our data indicate strong synergism between heat and PS at concentrations between 100 and 1000 nM, which is well within the range of plasma PS levels measured in adult humans (0.1-0.8 µM Havlikova et al., 2002). Plasma PS levels can rise to supramicromolar concentrations during parturition and under various pathological conditions but also decreases with aging (Havlikova et al., 2002; Hill et al., 2001; Schumacher et al., 2008), which may further influence heat sensitivity and pain through TRPM3.

In conclusion, we have identified TRPM3 as nociceptor channel involved in acute heat sensing and inflammatory heat hyperalgesia, and thus as a potential target for novel analgesic treatments.

MATERIALS AND METHODS

Cells

Human embryonic kidney cells, HEK293T, were grown in Dulbecco's modified Eagle's medium (DMEM) containing 10% (v/v) human serum, 2 mM L-glutamine, 2 units/ml penicillin, and 2 mg/ml streptomycin at 37° C. in a humidity-controlled incubator with 10% $CO_2$. HEK293T cells were transiently transfected with murine TRPM3α2 (accession number AJ 544535) in the bicistronic pCAGGS/IRES-GFP vector, using Mirus TransIT-293 (Mirus corporation; Madison USA). Transfected cells were visualized by green fluorescence protein (GFP) expression whereas GFP negative cells from the same batch were used as controls. TG and DRG neurons from adult (postnatal weeks 8-12) male mice were isolated as described previously (Karashima et al., 2007). HEK293T cells stably transfected with TRPM3α2 were developed using the Flp-In System (Invitrogen).

Animals

Trpm3$^{-/-}$ mice (FIG. 10), obtained from Lexicon Genetics (see http://www.informatics.iax.orp/searches/accession_report.cgi?id=MGI:3528836), were generated using homologous recombination in 129SvEvBrd ES cells. ES cells were injected into blastocysts from C57BL/6J donor mice to generate chimeric animals, which were mated with C57BL/6J mice and genotyped for the mutated allele. Heterozygotes were mated, resulting in Trpm3$^{+/+}$, Trpm3$^{+/-}$ and Trpm3$^{-/-}$ mice with the expected Mendelian distribution. Unless mentioned otherwise, paired Trpm3$^{+/+}$ and Trpm3$^{-/-}$ littermates were used in behavioral experiments. For comparison, we also used age-matched pure 129SvEvBrd (kindly provided by The Sanger Institute, Cambridge, UK) and C57BL/6J (Charles River) mice in behavioral experiments, as indicated in the text.

Trpv1$^{-/-}$ mice in pure C57BL/6J background were obtained from The Jackson Laboratory (http://jaxmice.jax-.org/strain/003770.html), and age- and weight-matched C57BL/6J mice were used as matched controls (Trpv1$^{+/+}$). Trpv1$^{-/-}$ mice were mated with Trpa1$^{-/-}$ mice (Kwan et al., 2006) to obtain Trpv1$^{-/-}$/Trpa1$^{-/-}$ double knockout mice.

Mice of all genotypes were housed under identical conditions, with a maximum of 4 animals per cage on a 12 h light-dark cycle and with food and water ad libitum. Only 10-12-weeks old male mice were used in all experiments.

Quantitative-PCR

Total RNA from freshly isolated DRG and TG tissues was extracted with the RNeasy mini kit (Qiagen) and subsequently served for cDNA synthesis using Ready-To-Go You-Prime first-strand beads (GE Healthcare). Triplicate cDNA samples from each independent preparation (n=3) were analyzed by quantitative real-time polymerase chain reactions (qPCR) in the 7500 Real-Time PCR system (Applied Biosystems) using specific TaqMan gene expression assays for Trpa1, Trpm3, Trpm8, Trpv1, Trpv2, Trpv3 And Trpv4 (Applied Biosystems). Glyceraldehyde 3-phosphate dehydrogenase (GAPDH) and β-actin were used as endogenous controls (Applied Biosystems). Trpv1 mRNA was used as a calibrator for relative quantifications of detected mRNA signals.

Protein Extraction and Immunodetection

Proteins from freshly isolated brain, DRG and TG tissues of wild type and Trpm3$^{-/-}$ mice were lysed in 3 ml ice-cold lysis buffer (50 mM Tris pH 7.5, 10 mM KCl, 1.5 mM MgCl$_2$, 1 mM EDTA, 1 mM phenylmethylsulfonyl fluoride (PMSF) and a protease inhibitors' cocktail (10 □g/ml leupeptin and antipain, 2 □g/ml chymostatin and pepstatin)) using the Polytron homogenizer (Kinematica AG, Switzerland). Obtained homogenates were centrifuged at 4000×g for 15 min to remove nuclei, mitochondria and any remaining large cellular fragments. Precleared supernatants were ultracentrifuged at 100000×g for 1 hour. Pellets containing total membrane fractions were solubilized in a cold phosphate-buffered saline (PBS; 10 mM phosphate buffer pH 7.4, 137 mM NaCl, 2.7 mM KCl,) containing 1% Triton X-100, 0.25% sodium dodecyl sulfate (SDS), 1 mM PMSF and a protease inhibitors' cocktail. Protein concentrations were determined by the bicinchoninic acid assay method, using bovine serum albumin (BSA) as a standard. Samples (30 μg) were subjected to SDS-polyacrylamide gel electrophoresis (SDS-PAGE) and subsequent transfer to a polyvinylidene fluoride (PVDF) membrane (Bio-Rad, USA) as previously described (Vriens et al., 2005). Respective proteins were detected with purified monoclonal rat anti-TRPM3 (1:600 dilution) (Wagner et al., 2008) and monoclonal mouse anti-Na$^+$/K$^+$ ATPase (1:5000 dilution) (Abcam, UK) antibodies. Immunoreactive complexes were visualized by chemiluminescence, using anti-rat IgG (Sigma, USA) or anti-mouse IgG (GE Healthcare) antibodies conjugated to horseradish peroxidase (1:40000 and 1:5000 dilutions, respectively).

Determination of Blood Glucose

Blood samples were collected via tail bleeding. Glucose levels were measured via the ACCU-CHEK Aviva blood glucose meter (Roche Diagnostics).

PhysioTel™ Telemetry System

An ETA-F10 Transmitter (DSI™, Minneapolis, USA) was implanted in the abdominal cavity (intraperitoneally) of an adult (postnatal weeks 10-12) male mice. Three weeks after surgery mice were recovered and used to perform experiments. Data were collected using DSI Dataquest® A.R.T.™ system ((DSI™, Minneapolis, USA). Body core temperature, heart rate and ECG were sampled every 2 s. Vehicle, pregnenolone sulphate and capsaicin were subcutaneously injected (200 μl) at the indicated concentrations.

In Situ Hybridization

Trigeminal ganglia (TG) and dorsal root ganglia (DRG) tissues from Trpm3$^{+/+}$ and Trpm3$^{-/-}$ mice were dissected and snap-frozen in the KP-CryoCompound medium (Klinipath, the Netherlands). 20 μm thick cryostat sections were processed and probed with digoxigenin (DIG)-labeled sense and antisense RNA probes. The RNA probes were generated by SP6/T7 in vitro transcription reactions (Roche Diagnostics), using cDNA fragments of Trpm3 (accession number AJ 544535, 348 base pairs (bp) between nucleotides 1531-1879), Trpv1 (accession number NM_001001445, 346 by between nucleotides 1157-1503). Hybrid molecules were detected with alkaline phosphatase-conjugated anti-DIG Fab fragments according to the manufacturer's instructions (Roche Diagnostics).

Electrophysiology and Intracellular Ca$^{2+}$ Assays

Whole-cell membrane currents were measured with an EPC-10 (HEKA Elektronik, Lambrecht, Germany). The sampling rate was 20 kHz and currents were digitally filtered at 2.9 kHz. For recordings on HEK293T cells, the extracellular solution contained (in mM): 138 NaCl, 5.4 KCl, 2 MgCl$_2$, 2 CaCl$_2$, 10 glucose, 10 HEPES (pH 7.2 with NaOH), and the pipette solution contained (in mM): 100 CsAsp, 45 CsCl, 10 EGTA, 10 HEPES, 1 MgCl (pH 7.2 with CsOH). For recordings on sensory neurons, the extracellular solution contained (in mM): 140 NaCl, 4 KCl, 2 MgCl$_2$, 100 nM TTX, 10 TRIS (pH 7.4 with HCl), and the pipette solution contained (in mM): 140 CsCl, 0.6 MgCl$_2$, 1 EGTA, 10 HEPES, 5 TEA (pH 7.2 with CsOH). To determine the I-V relationship of PS induced currents in neurons, all measurements were performed under monovalent free extracellular conditions in order to suppress other cationic conductances present in DRG neurons. The extracellular solution contained in mM 2 CaCl$_2$, 2 MgCl$_2$, 10 HEPES, 280 D-Mannitol (pH 7.2 with NMDG).

Fura-2-based ratiometric intracellular Ca$^{2+}$ measurements were performed as described previously (Vriens et al., 2007). The following procedure was used to distinguish stimulus-induced responses from background variations in fluorescence. First, we calculated the time derivative of the fluorescence ratio (dRatio/dt), and the standard deviation (SD) of dRatio/dt in the absence of any stimulus. A positive response was noted when a stimulus caused an increase of dRatio/dt exceeding 5×SD. Non-responsive neurons that also failed to response to 50 mM K$^+$ were discarded from analysis. For every condition, a minimum of 100 cells derived from at least three separated isolations and in at least twelve independent measurements were analyzed.

To determine an average temperature-response relation for TRPM3, we also used a fluo-4-based assay using 96 well plates and the 7500 Real-Time PCR system (Applied Biosystems). HEK293T cells stably expressing murine TRPM3α2 (FIG. 9B) or non transfected HEK293T cells were loaded with Fluo-4-AM for 30 min, trypsinized, centrifuged, resuspended in a solution containing (in mM) 150 NaCl, 6 KCl, 2 MgCl$_2$, 2 CaCl$_2$, and 10 HEPES (pH 7.4 with NaOH) and transferred to a 96-well plate (at 15000-25000 cells/well; 50 μl). When indicated, PS (10 μM) was added to the wells. Fluo-4 fluorescence was measured while the well temperature was raised from 16 to 43° C. in 3-degrees steps. Background-subtracted fluorescence signals were used to calculate temperature-induced changes in fluorescence as ΔF/F$_{16°C}$, where F$_{16°C}$ is the background corrected fluorescence at 16° C. and ΔF=F−F$_{16°C}$. The neurosteroids pregnenolone sulphate, progesterone and the TRPV1 activator capsaicin (all Sigma) were applied at indicated concentrations from a respectively 100 mM, 250 mM and 10 mM stock solution in DMSO.

Behavior

Hind paw injections, drinking tests, thermal gradient tests, temperature choice tests, hot plate, cold plate, tail clip and tail immersion assays were performed as previously described (Cao et al., 1998; Caterina et al., 2000; Karashima et al., 2009;

Mocrich et al., 2005). To evoke inflammatory hyperalgesia, Complete Freund's Adjuvant (CFA, Sigma) (50 μl) was injected intraplantarly in both hindpaws 24 h before behavioral testing. Corn oil was used as vehicle control. To obtain pharmacological inhibition of TRPV1, AMG 9810 (Tocris Bioscience) dissolved in DMSO was injected i.p at 3 mg/kg during consecutive 7 days (Gavva et al., 2007; Gavva et al., 2005). DMSO was used as vehicle control. All animal experiments were carried out in accordance with the European Union Community Council guidelines and were approved by the local ethics committee.

Data Analysis

Electrophysiological data were analyzed using FITMASTER (HEKA Elektronik, Germany) and WinASCD software (Guy Droogmans, Leuven). Origin 7.1 (OriginLab Corporation, Northampton, USA) was used for statistical analysis and data display. The parameters for the two-state model were determined from a global fit of simulated whole-cell currents to experimental currents measured during voltage steps at different temperatures (FIG. 5), using home-made routines in Igor Pro 5.0 (Karashima et al., 2009; Voets et al., 2004; Voets et al., 2007). We assumed a linear single channel conductance with a $Q_{10}$ value of 1.35

Pooled data of continuous parameters are expressed as mean±SEM, and Student's unpaired, two-tailed t-test was used for statistical comparison between groups. Fisher's exact test was used to detect statistical differences in the fraction of responders between genotypes. $P<0.05$ was considered statistically significant.

REFERENCES

Bandell, M., Macpherson, L. J., and Patapoutian, A. (2007). From chills to chilis: mechanisms for thermosensation and chemesthesis via thermoTRPs. Curr Opin Neurobiol 17, 490-497.

Basbaum, A. I., Bautista, D. M., Scherrer, G., and Julius, D. (2009). Cellular and molecular mechanisms of pain. Cell 139, 267-284.

Bautista, D. M., Jordt, S. E., Nikai, T., Tsuruda, P. R., Read, A. J., Poblete, J., Yamoah, E. N., Basbaum, A. I., and Julius, D. (2006). TRPA1 mediates the inflammatory actions of environmental irritants and proalgesic agents. Cell 124, 1269-1282.

Bautista, D. M., Siemens, J., Glazer, J. M., Tsuruda, P. R., Basbaum, A. I., Stucky, C. L., Jordt, S. E., and Julius, D. (2007). The menthol receptor TRPM8 is the principal detector of environmental cold. Nature 448, 204-208.

Cao, Y. Q., Mantyh, P. W., Carlson, E. J., Gillespie, A. M., Epstein, C. J., and Basbaum, A. I. (1998). Primary afferent tachykinins are required to experience moderate to intense pain. Nature 392, 390-394.

Caterina, M. J. (2007). Transient receptor potential ion channels as participants in thermosensation and thermoregulation. Am J Physiol Regul Integr Comp Physiol 292, R64-76.

Caterina, M. J., Leffler, A., Malmberg, A. B., Martin, W. J., Trafton, J., Petersen-Zeitz, K. R., Koltzenburg, M., Basbaum, A. I., and Julius, D. (2000). Impaired nociception and pain sensation in mice lacking the capsaicin receptor. Science 288, 306-313.

Caterina, M. J., Rosen, T. A., Tominaga, M., Brake, A. J., and Julius, D. (1999). A capsaicin-receptor homologue with a high threshold for noxious heat. Nature 398, 436-441

Caterina, M. J., Schumacher, M. A., Tominaga, M., Rosen, T. A., Levine, J. D., and Julius, D. (1997). The capsaicin receptor: a heat-activated ion channel in the pain pathway. Nature 389, 816-824.

Chen, S. C., and Wu, F. S. (2004). Mechanism underlying inhibition of the capsaicin receptor-mediated current by pregnenolone sulfate in rat dorsal root ganglion neurons. Brain Res 1027, 196-200.

Chung, M. K., Lee, H., and Caterina, M. J. (2003). Warm temperatures activate TRPV4 in mouse 308 keratinocytes. J Biol Chem 278, 32037-32046.

Chung, M. K., Lee, H., Mizuno, A., Suzuki, M., and Caterina, M. J. (2004). TRPV3 and TRPV4 mediate warmth-evoked currents in primary mouse keratinocytes. J Biol Chem 279, 21569-21575.

Colburn, R. W., Lubin, M. L., Stone, D. J., Jr., Wang, Y., Lawrence, D., D'Andrea, M. R., Brandt, M. R., Liu, Y., Flores, C. M., and Qin, N. (2007). Attenuated cold sensitivity in TRPM8 null mice. Neuron 54, 379-386.

Damann, N., Voets, T., and Nilius, B. (2008). TRPs in our senses. Curr Biol 18, R880-889.

Davis, J. B., Gray, J., Gunthorpe, M. J., Hatcher, J. P., Davey, P. T., Overend, P., Harries, M. H., Latcham, J., Clapham, C., Atkinson, K., et al. (2000). Vanilloid receptor-1 is essential for inflammatory thermal hyperalgesia. Nature 405, 183-187.

Dhaka, A., Murray, A. N., Mathur, J., Earley, T. J., Petrus, M. J., and Patapoutian, A. (2007). TRPM8 is required for cold sensation in mice. Neuron 54, 371-378.

Fajardo, O., Meseguer, V., Belmonte, C., and Viana, F. (2008). TRPA1 channels: novel targets of 1,4-dihydropyridines. Channels (Austin) 2, 429-438.

Fischbach, T., Greffrath, W., Nawrath, H., and Treede, R. D. (2007). Effects of anandamide and noxious heat on intracellular calcium concentration in nociceptive drg neurons of rats. J Neurophysiol 98, 929-938.

Gavva, N. R., Bannon, A. W., Hovland, D. N., Jr., Lehto, S. G., Klionsky, L., Surapaneni, S., Immke, D. C., Henley, C., Arik, L., Bak, A., et al. (2007). Repeated administration of vanilloid receptor TRPV1 antagonists attenuates hyperthermia elicited by TRPV1 blockade. J Pharmacol Exp Ther 323, 128-137.

Gavva, N. R., Tamir, R., Qu, Y., Klionsky, L., Zhang, T. J., Immke, D., Wang, J., Zhu, D., Vanderah, T. W., Porreca, F., et al. (2005). AMG 9810 [(E)-3-(4-t-butylphenyl)-N-(2,3-dihydrobenzo[b][1,4]dioxin-6-yl)acrylamide], a novel vanilloid receptor 1 (TRPV1) antagonist with antihyperalgesic properties. J Pharmacol Exp Ther 313, 474-484.

Grimm, C., Kraft, R., Sauerbruch, S., Schultz, G., and Harteneck, C. (2003). Molecular and functional characterization of the melastatin-related cation channel TRPM3. J Biol Chem 278, 21493-21501.

Grimm, C., Kraft, R., Schultz, G., and Harteneck, C. (2005). Activation of the melastatin-related cation channel TRPM3 by D-erythro-sphingosine [corrected]. Mol Pharmacol 67, 798-805.

Guler, A. D., Lee, H., Iida, T., Shimizu, I., Tominaga, M., and Caterina, M. (2002). Heat-evoked activation of the ion channel, TRPV4. J Neurosci 22, 6408-6414.

Havlikova, H., Hill, M., Hampl, R., and Starka, L. (2002). Sex- and age-related changes in epitestosterone in relation to pregnenolone sulfate and testosterone in normal subjects. J Clin Endocrinol Metab 87, 2225-2231.

Hill, M., Bicikova, M., Parizek, A., Havlikova, H., Klak, J., Fajt, T., Meloun, M., Cibula, D., Cegan, A., Sulcova, J., et al. (2001). Neuroactive steroids, their precursors and polar conjugates during parturition and postpartum in maternal blood: 2. Time profiles of pregnanolone isomers. J Steroid Biochem Mol Biol 78, 51-57.

Karashima, Y., Damann, N., Prenen, J., Talavera, K., Segal, A., Voets, T., and Nilius, B. (2007). Bimodal action of menthol on the transient receptor potential channel TRPA1. J Neurosci 27, 9874-9884.

Karashima, Y., Talavera, K., Everaerts, W., Janssens, A., Kwan, K. Y., Vennekens, R., Nilius, B., and Voets, T. (2009). TRPA1 acts as a cold sensor in vitro and in vivo. Proc Natl Acad Sci USA 106, 1273-1278.

Knowlton, W. M., Bifolck-Fisher, A., Bautista, D. M., and McKemy, D. D. (2010). TRPM8, but not TRPA1, is required for neural and behavioral responses to acute noxious cold temperatures and cold-mimetics in vivo. Pain 150, 340-350.

Kwan, K. Y., Allchorne, A. J., Vollrath, M. A., Christensen, A. P., Zhang, D. S., Woolf, C. J., and Corey, D. P. (2006). TRPA1 contributes to cold, mechanical, and chemical nociception but is not essential for hair-cell transduction. Neuron 50, 277-289.

Lechner, S. G., Frenzel, H., Wang, R., and Lewin, G. R. (2009). Developmental waves of mechanosensitivity acquisition in sensory neuron subtypes during embryonic development. Embo J 28, 1479-1491.

Lee, H., Iida, T., Mizuno, A., Suzuki, M., and Caterina, M. J. (2005). Altered thermal selection behavior in mice lacking transient receptor potential vanilloid 4. J Neurosci 25, 1304-1310.

Lee, N., Chen, J., Sun, L., Wu, S., Gray, K. R., Rich, A., Huang, M., Lin, J. H., Feder, J. N., Janovitz, E. B., et al. (2003). Expression and characterization of human transient receptor potential melastatin 3 (hTRPM3). J Biol Chem 278, 20890-20897.

Madrid, R., de la Pena, E., Donovan-Rodriguez, T., Belmonte, C., and Viana, F. (2009). Variable threshold of trigeminal cold-thermosensitive neurons is determined by a balance between TRPM8 and Kv1 potassium channels. J Neurosci 29, 3120-3131.

McKemy, D. D., Neuhausser, W. M., and Julius, D. (2002). Identification of a cold receptor reveals a general role for TRP channels in thermosensation. Nature 416, 52-58.

Mogil, J. S., Wilson, S. G., Bon, K., Lee, S. E., Chung, K., Raber, P., Pieper, J. O., Hain, H. S., Belknap, J. K., Hubert, L., et al. (1999). Heritability of nociception I: responses of 11 inbred mouse strains on 12 measures of nociception. Pain 80, 67-82.

Moqrich, A., Hwang, S. W., Earley, T. J., Petrus, M. J., Murray, A. N., Spencer, K. S., Andahazy, M., Story, G. M., and Patapoutian, A. (2005). Impaired thermosensation in mice lacking TRPV3, a heat and camphor sensor in the skin. Science 307, 1468-1472.

Naylor, J., Li, J., Milligan, C. J., Zeng, F., Sukumar, P., Hou, B., Sedo, A., Yuldasheva, N., Majeed, Y., Beni, D., et al. (2010). Pregnenolone Sulphate- and Cholesterol-Regulated TRPM3 Channels Coupled to Vascular Smooth Muscle Secretion and Contraction. Circ Res.

Nealen, M. L., Gold, M. S., Thut, P. D., and Caterina, M. J. (2003). TRPM8 mRNA is expressed in a subset of cold-responsive trigeminal neurons from rat. J Neurophysiol 90, 515-520.

Nilius, B., and Voets, T. (2007). Neurophysiology: channelling cold reception. Nature 448, 147-148.

Nilius, B., and Voets, T. (2008). A TRP channel-steroid marriage. Nat Cell Biol 10, 1383-1384.

Noel, J., Zimmermann, K., Busserolles, J., Deval, E., Alloui, A., Diochot, S., Guy, N., Borsotto, M., Reeh, P., Eschalier, A., and Lazdunski, M. (2009). The mechano-activated K+ channels TRAAK and TREK-1 control both warm and cold perception. Embo J 28, 1308-1318.

Oberwinkler, J., L is, A., Giehl, K. M., Flockerzi, V., and Philipp, S. E. (2005). Alternative splicing switches the divalent cation selectivity of TRPM3 channels. J Biol Chem 280, 22540-22548.

Oberwinkler, J., and Philipp, S. E. (2007). Trpm3. Handb Exp Pharmacol, 253-267.

Peier, A. M., Moqrich, A., Hergarden, A. C., Reeve, A. J., Andersson, D. A., Story, G. M., Earley, T. J., Dragoni, I., McIntyre, P., Bevan, S., and Patapoutian, A. (2002a). A TRP channel that senses cold stimuli and menthol. Cell 108, 705-715.

Peier, A. M., Reeve, A. J., Andersson, D. A., Moqrich, A., Earley, T. J., Hergarden, A. C., Story, G. M., Colley, S., Hogenesch, J. B., McIntyre, P., et al. (2002b). A heat-sensitive TRP channel expressed in keratinocytes. Science 296, 2046-2049.

Reubish, D., Emerling, D., Defalco, J., Steiger, D., Victoria, C., and Vincent, F. (2009). Functional assessment of temperature-gated ion-channel activity using a real-time PCR machine. Biotechniques 47, iii-ix.

Schumacher, M., Liere, P., Akwa, Y., Rajkowski, K., Griffiths, W., Bodin, K., Sjovall, J., and Baulieu, E. E. (2008). Pregnenolone sulfate in the brain: a controversial neurosteroid. Neurochem Int 52, 522-540.

Smith, G. D., Gunthorpe, M. J., Kelsell, R. E., Hayes, P. D., Reilly, P., Facer, P., Wright, J. E., Jerman, J. C., Walhin, J. P., Ooi, L., et al. (2002). TRPV3 is a temperature-sensitive vanilloid receptor-like protein. Nature 418, 186-190.

Staaf, S., Franck, M. C., Marmigere, F., Mattsson, J. P., and Ernfors, P. (2010). Dynamic expression of the TRPM subgroup of ion channels in developing mouse sensory neurons. Gene Expr Patterns 10, 65-74.

Story, G. M., Peier, A. M., Reeve, A. J., Eid, S. R., Mosbacher, J., Hricik, T. R., Earley, T. J., Hergarden, A. C., Andersson, D. A., Hwang, S. W., et al. (2003). ANKTM1, a TRP-like channel expressed in nociceptive neurons, is activated by cold temperatures. Cell 112, 819-829.

Talavera, K., Nilius, B., and Voets, T. (2008). Neuronal TRP channels: thermometers, pathfinders and life-savers. Trends Neurosci 31, 287-295.

Talavera, K., Yasumatsu, K., Voets, T., Droogmans, G., Shigemura, N., Ninomiya, Y., Margolskee, R. F., and Nilius, B. (2005). Heat activation of TRPM5 underlies thermal sensitivity of sweet taste. Nature 438, 1022-1025.

Togashi, K., Hara, Y., Tominaga, T., Higashi, T., Konishi, Y., Mori, Y., and Tominaga, M. (2006). TRPM2 activation by cyclic ADP-ribose at body temperature is involved in insulin secretion. Embo J 25, 1804-1815.

Tominaga, M., Caterina, M. J., Malmberg, A. B., Rosen, T. A., Gilbert, H., Skinner, K., Raumann, B. E., Basbaum, A. I., and Julius, D. (1998). The cloned capsaicin receptor integrates multiple pain-producing stimuli. Neuron 21, 531-543.

Ueda, H., Inoue, M., Yoshida, A., Mizuno, K., Yamamoto, H., Maruo, J., Matsuno, K., and Mita, S. (2001). Metabotropic neurosteroid/sigma-receptor involved in stimulation of nociceptor endings of mice. J Pharmacol Exp Ther 298, 703-710.

Viana, F., de la Pena, E., and Belmonte, C. (2002). Specificity of cold thermotransduction is determined by differential ionic channel expression. Nat Neurosci 5, 254-260.

Voets, T., Droogmans, G., Wissenbach, U., Janssens, A., Flockerzi, V., and Nilius, B. (2004). The principle of temperature-dependent gating in cold- and heat-sensitive TRP channels. Nature 430, 748-754.

Voets, T., Owsianik, G., Janssens, A., Talayera, K., and Nilius, B. (2007). TRPM8 voltage sensor mutants reveal a mechanism for integrating thermal and chemical stimuli. Nature Chemical Biology 3, 174-182.

Vriens, J., Owsianik, G., Fisslthaler, B., Suzuki, M., Janssens, A., Voets, T., Morisseau, C., Hammock, B. D., Fleming, I., Busse, R., and Nilius, B. (2005). Modulation of the $Ca^{2+}$ permeable cation channel TRPV4 by cytochrome P450 epoxygenases in vascular endothelium. Circ Res 97, 908-915.

Vriens, J., Owsianik, G., Janssens, A., Voets, T., and Nilius, B. (2007). Determinants of 4 alpha-phorbol sensitivity in transmembrane domains 3 and 4 of the cation channel TRPV4. J Biol Chem 282, 12796-12803.

Wagner, T. F., Loch, S., Lambert, S., Straub, I., Mannebach, S., Mathar, I., Dufer, M., L is, A., Flockerzi, V., Philipp, S. E., and Oberwinkler, J. (2008). Transient receptor potential M3 channels are ionotropic steroid receptors in pancreatic beta cells. Nat Cell Biol 10, 1421-1430.

Watanabe, H., Vriens, J., Suh, S. H., Benham, C. D., Droogmans, G., and Nilius, B. (2002). Heat-evoked activation of TRPV4 channels in a HEK293 cell expression system and in native mouse aorta endothelial cells. J Biol Chem 277, 47044-47051.

Woodbury, C. J., Zwick, M., Wang, S., Lawson, J. J., Caterina, M. J., Koltzenburg, M., Albers, K. M., Koerber, H. R., and Davis, B. M. (2004). Nociceptors lacking TRPV1 and TRPV2 have normal heat responses. J Neurosci 24, 6410-6415.

Xu, H., Ramsey, I. S., Kotecha, S. A., Moran, M. M., Chong, J. A., Lawson, D., Ge, P., Lilly, J., Silos-Santiago, I., Xie, Y., et al. (2002). TRPV3 is a calcium-permeable temperature-sensitive cation channel. Nature 418, 181-186.

What is claimed is:

1. A method for identifying an agent suitable for the treatment and/or prophylaxis of pain, wherein said method comprises:
    identifying a TRPM3 antagonist by screening for an agent for its ability to inhibit TRPM3, wherein the screening comprises:
        (i) contacting a TRPM3-expressing cell with a candidate TRPM3 antagonist, and
        (ii) determining that the candidate TRPM3 antagonist inhibits TRPM3, thereby identifying the candidate TRPM3 antagonist as the TRPM3 antagonist;
    providing said TRPM3 antagonist in a pharmaceutical composition in a formulation suitable for the treatment and/or prophylaxis of pain,
    delivering the pharmaceutical composition to a subject, and
    identifying said TRPM3 antagonist as the agent suitable for the treatment and/or prophylaxis of pain by identifying an antinociceptive response in the subject.

2. The method according to claim 1, wherein said method comprises determining whether said agent is capable of inhibiting expression of a gene encoding TRPM3, or capable of inhibiting expression of a TRPM3 agonist.

3. The method according to claim 1, wherein said determining comprises the steps of:
    (a) loading TRPM3-expressing cells with a labeled compound that is capable of monitoring TRPM3 activity;
    (b) incubating a first group of said loaded TRPM3-expressing cells from step (a) with said candidate TRPM3 antagonists, and incubating a second group, non-treated cells, of said loaded TRPM3-expressing cells from step (a) with vehicle, not containing the candidate TRPM3 antagonist;
    (c) stimulating TRPM3 activity with a TRPM3 activating stimulus; and
    (d) measuring and comparing a signal from the labeled compound between cells incubated with candidate TRPM3 antagonists and non-treated cells, wherein a decrease of the signal in the first group of cells, the candidate TRPM3 antagonist-treated cells, compared to the second group of cells, the untreated cells, indicate the agent as a TRPM3 antagonist.

4. The method according to claim 1, wherein said determining comprises the steps of:
    (a) measuring whole-cell patch-clamp recordings on TRPM3-expressing cells, wherein whole-cell currents are measured (1) under basal conditions, (2) after stimulation with a TRPM3-activating stimulus (3) and after addition of said candidate TRPM3 antagonists in a first group, or vehicle in a second group, both groups in the continued presence of said activating stimulus; and
    (b) comparing the remaining whole-cell current between cells treated with the candidate TRPM3 antagonist and cells treated with vehicle, untreated cells, wherein a decrease of the whole-cell current in the first group of cells, the candidate TRPM3 antagonist treated cells, compared to the second group of cells, the untreated cells, indicate the agent as a TRPM3 antagonist.

5. The method according to claim 1, wherein the subject is a laboratory animal and wherein said identifying comprises the steps of:
    (a) applying said TRPM3-antagonists to a first group of laboratory animals and a vehicle treated second group, untreated group, of laboratory animals;
    (b) injecting the laboratory animals locally with a suitable TRPM3 agonist; and
    (c) measuring and comparing the nociceptive response to agonist injection, by monitoring nocifensive behaviour, between animals treated with said TRPM3-antagonist and animals treated with vehicle, untreated group, wherein a decrease of the nociceptive response in the first group, the TRPM3 antagonist treated laboratory animals compared to the second group of vehicle treated laboratory animals, the untreated group, identify the agent as a TRPM3 antagonist suitable for the treatment and/or prophylaxis of pain.

6. The method according to claim 1, wherein the subject is a laboratory animal and wherein said identifying comprises the steps of:
    (a) applying said TRPM3-antagonists to a first group of laboratory animals and a vehicle treated, untreated, second group of laboratory animals; and
    (b) measuring and comparing the nociceptive response to a heat stimulus between the group of animals treated with said TRPM3-antagonist and the group of animals treated with vehicle, untreated group, wherein a decrease of the nociceptive response in the first group, the TRPM3 antagonist treated laboratory animals, compared to the second group of vehicle treated laboratory animals identify the agent as a TRPM3 antagonist suitable for the treatment and/or prophylaxis of pain.

7. The method according to claim 1, wherein the subject is a laboratory animal and wherein said identifying comprises the steps of:
    (a) measuring the nociceptive response in said laboratory animals to a heat stimulus;
    (b) inducing local inflammation in said laboratory animals;
    (c) applying said TRPM3-antagonists to said laboratory animals of step (b);

(d) measuring the nociceptive response of the TRPM-3 antagonist treated laboratory animals of step (c) to a heat stimulus; and
(e) comparing the nociceptive response in the second heat-treated animals of step (d), with the nociceptive response to the first heat-treated animals of step (a), wherein a decrease or status quo of the nociceptive response in the second heat treated group of step (d) compared to the first heat treated group of step (a), identify the agent as a TRPM3 antagonist antagonist suitable for the treatment and/or prophylaxis of pain.

* * * * *